(12) United States Patent
Bonda et al.

(10) Patent No.: US 6,919,473 B2
(45) Date of Patent: Jul. 19, 2005

(54) PHOTOSTABILIZERS, UV ABSORBERS, AND METHODS OF PHOTOSTABILIZING A SUNSCREEN COMPOSITION

(75) Inventors: Craig A. Bonda, Winfield, IL (US); Anna B. Pavlovic, Elmwood Park, IL (US)

(73) Assignee: CPH Innovations Corporation, Chicago, IL (US)

( * ) Notice: Subject to any disclaimer, the term of this patent is extended or adjusted under 35 U.S.C. 154(b) by 0 days.

(21) Appl. No.: 10/458,286

(22) Filed: Jun. 10, 2003

(65) Prior Publication Data

US 2004/0062726 A1 Apr. 1, 2004

Related U.S. Application Data

(63) Continuation-in-part of application No. 10/246,434, filed on Sep. 17, 2002.

(51) Int. Cl.$^7$ ............................................. C07C 69/76
(52) U.S. Cl. ............................................. 560/8; 560/19
(58) Field of Search ...................................... 560/8, 19

(56) References Cited

U.S. PATENT DOCUMENTS

| | | | | |
|---|---|---|---|---|
| 3,215,724 A | 11/1965 | Strobel et al. | ............... | 260/465 |
| 3,215,725 A | 11/1965 | Strobel et al. | ............... | 260/465 |
| 3,272,855 A | 9/1966 | Strobel et al. | ............... | 260/465 |

(Continued)

FOREIGN PATENT DOCUMENTS

| | | |
|---|---|---|
| CA | 1 164 886 | 4/1984 |
| CA | 2204430 | 5/1996 |
| DE | 31 06 071 | 2/1982 |
| DE | 44 40 055 | 5/1996 |
| DE | 195 19 895 | 12/1996 |
| DE | 196 30 479 | 1/1998 |
| DE | 10008895 | 8/2001 |
| DE | 100 15 863 | 10/2001 |
| DE | 100 26 628 | 12/2001 |
| DE | 100 58 290 | 5/2002 |
| EP | 0 675 875 | 11/1998 |
| EP | 0 900 782 | 3/1999 |
| EP | 1129696 | 9/2001 |
| EP | 1 308 084 | 5/2003 |
| GB | 1129029 | 10/1968 |
| JP | 56-140959 | 4/1981 |
| WO | WO 94/14760 | 7/1994 |
| WO | WO 96/15102 | 5/1996 |
| WO | WO 00/44340 | 8/2000 |
| WO | WO 01/16224 | 3/2001 |
| WO | WO 01/57125 | 8/2001 |
| WO | WO 01/90233 | 11/2001 |
| WO | WO 01/92395 | 12/2001 |
| WO | WO 02/42368 | 5/2002 |
| WO | WO 2004/031294 | 4/2004 |

OTHER PUBLICATIONS

CA 131:25731 for Yokota et al, JP 11143095 (1999).*
CA 128:204935 for Bettencourt et al, Journal of the Chemical Society, Perkins, 2, (1998), 3, pp. 515–522.*
CA 126:96893 for YAmada et al, JP 08262759 (1996).*
CA 131:25731 for Yokota, JP 11143095, (1999).*
CA 128:204935 for Bettencourt et al, Journal of the Chemical Society, Perkins, 2 (1998) (3) pp515–522.*
CA 126:96893 for Yamada et al, JP 08262759 (1996).*
International Search Report dated Dec. 13, 2004, from the European Patent Office (ISA) in counterpart International Application No. PCT/US2004/016761.
Written Opinion dated Dec. 13, 2004, from the European Patent Office (ISA) in counterpart International Application No. PCT/US2004/016761.
Lehnert, Knoevenagel–Kondensationen Mit TiCl$_4$/BASE–III$^1$ Tetrahedron vol. 29, pp. 635–638 (1973).
Wittig et al., "zur Umkehrbarkeit von Kondensationsrektionen in alkalischen Medium", Chemische Berichte, p. 117, lines 13–21, vol. 83 (1950).
"Photostability of HallStar Photostable SPF 32 Sunscreen Compared to Neutrogena UVA/UVB Sunblock SPF 30," Suncare Research Laboratories, Memphis, Tennessee (Oct. 5, 2000).
Beckwith, in "The chemistry of amides: Synthesis of amides," Zabicky, J., Ed. Interscience: New York, pp. 73–185 (1970).
Bentley et al., "Medium Effects on the Rates and Mechanisms of Solvolytic Reactions," *Adv. Phys. Org. Chem.*, vol. 14, pp. 1–67 (1977).
Bentley et al., "Yx Scales of Solvent Ionizing Power," *Progr. Phys. Org. Chem.*, vol. 17, pp. 121–158 (1990).
Dimroth et al., Über Pyridinium–N–Phenol–Betaine und Ihre Ver Wendung Zur Charakterisierisierung Der Polarität Von Lösungsmitteln *Justus Liebigs Ann. Chem.*, vol. 661 pp. 1–37 (1963).
Fainberg et al., "Correlation of Solvolysis Rates. III. t–Butyl Chloride in a Wide Range of Solvent Mixtures," *J. Am Chem. Soc.*, vol. 78 pp. 2770–2777 (1956).
Grunwald et al., "The Correlation of Solvolysis Rates," J. Am. Chem. Soc., vol. 70, pp. 846–854 (1948).

(Continued)

*Primary Examiner*—Cecilia J. Tsang
*Assistant Examiner*—Hector M. Reyes
(74) *Attorney, Agent, or Firm*—Marshall, Gerstein & Borun LLP

(57) ABSTRACT

Derivatives of fluorene, including ester derivatives of cyano (9H-fluoren-9-ylidene) acetic acid, and sunscreen compositions including a mixture of a photoactive compound and an ester derivative of cyano(9H-fluoren-9-ylidene) acetic acid are disclosed herein. Also disclosed are methods for terminating a polymer chain with an ester derivative of cyano (9H-fluoren-9-ylidene) acetic acid and methods of filtering out ultra-violet light from a substrate by the use of one or more such derivatives.

6 Claims, 8 Drawing Sheets

U.S. PATENT DOCUMENTS

| | | |
|---|---|---|
| 3,275,520 A | 9/1966 | Strobel et al. .................. 167/90 |
| 3,337,357 A | 8/1967 | Strobel et al. ................ 106/178 |
| 3,445,545 A | 5/1969 | Skoultchi ..................... 260/881 |
| 3,461,108 A | 8/1969 | Heilman et al. ............ 260/78.5 |
| 3,560,455 A | 2/1971 | Hazen et al. ................ 526/272 |
| 3,560,456 A | 2/1971 | Hazen et al. ................ 526/272 |
| 3,560,457 A | 2/1971 | Hazen et al. ................ 526/272 |
| 3,580,893 A | 5/1971 | Heilman ...................... 525/384 |
| 3,706,704 A | 12/1972 | Heilman ...................... 526/208 |
| 3,729,450 A | 4/1973 | Galiano et al. .............. 528/500 |
| 3,729,451 A | 4/1973 | Blecke et al. ............. 260/78.5 |
| 3,860,700 A | 1/1975 | Viout et al. ..................... 424/61 |
| RE28,475 E | 7/1975 | Blecke et al. ............. 260/78.5 |
| 3,992,356 A | 11/1976 | Jacquet et al. ................. 260/47 |
| 4,069,046 A | 1/1978 | Hoegl et al. ......................... 96/1 |
| 4,107,290 A | 8/1978 | Jacquet et al. ................. 424/47 |
| 4,128,536 A | 12/1978 | Brodsky et al. ............... 427/54 |
| 4,178,303 A | 12/1979 | Lorenz et al. ............... 260/465 |
| 4,202,834 A | 5/1980 | Gruber et al. ............... 260/465 |
| 4,202,836 A | 5/1980 | Gruber et al. ........... 260/465.4 |
| 4,203,919 A | 5/1980 | Gruber et al. ............... 260/465 |
| 4,207,253 A | 6/1980 | Lorenz et al. ............... 260/465 |
| 4,218,392 A | 8/1980 | Lorenz et al. ............... 260/465 |
| 4,247,475 A | 1/1981 | Ching ........................ 260/465 |
| 4,260,719 A | 4/1981 | Ching ........................ 528/196 |
| 4,263,366 A | 4/1981 | Lorenz et al. ............... 428/332 |
| 4,264,680 A | 4/1981 | Anthony ..................... 428/412 |
| 4,276,136 A | 6/1981 | Gruber et al. ............... 204/159 |
| 4,387,089 A | 6/1983 | De Polo ...................... 424/59 |
| 4,489,057 A | 12/1984 | Welters et al. ................ 424/47 |
| 4,562,067 A | 12/1985 | Hopp et al. .................... 424/59 |
| 4,868,246 A | 9/1989 | MacLeay et al. ........... 525/142 |
| 5,013,777 A | 5/1991 | MacLeay et al. ........... 524/159 |
| 5,096,977 A | 3/1992 | MacLeay et al. ........... 525/343 |
| 5,210,275 A | 5/1993 | Sabatelli ...................... 560/43 |
| 5,321,112 A | 6/1994 | Olson .......................... 528/75 |
| 5,576,354 A | 11/1996 | Deflandre et al. ........... 514/685 |
| 5,681,871 A | 10/1997 | Molock et al. ............. 523/106 |
| 5,821,380 A | 10/1998 | Holderbaum et al. ....... 558/443 |
| 5,869,099 A | 2/1999 | Keller et al. ................ 424/486 |
| 5,882,633 A | 3/1999 | Pisson et al. .................. 424/59 |
| 5,972,324 A | 10/1999 | Zofchak et al. .......... 424/78.03 |
| 5,993,789 A | 11/1999 | Bonda et al. .................. 424/59 |
| 6,001,337 A | 12/1999 | Keller et al. .................. 424/59 |
| 6,033,649 A | 3/2000 | Gonzenbach et al. ......... 424/60 |
| 6,126,925 A | 10/2000 | Bonda et al. .................. 424/59 |
| 6,143,850 A | 11/2000 | Keller et al. ................ 526/304 |
| 6,224,854 B1 | 5/2001 | Robinson ..................... 424/59 |
| 6,284,916 B1 | 9/2001 | Bonda et al. .................. 560/80 |
| 6,297,300 B1 | 10/2001 | Van Nuffel .................. 524/91 |
| 6,306,507 B1 | 10/2001 | Brunelle et al. ......... 428/423.7 |
| 6,358,892 B1 | 3/2002 | Harrison et al. ............ 508/192 |
| 6,365,311 B1 | 4/2002 | Wilson et al. ........... 430/108.2 |
| 6,416,773 B2 | 7/2002 | Heidenfelder et al. ...... 424/401 |
| 6,441,071 B1 | 8/2002 | Van Nuffel ................ 524/316 |
| 6,485,713 B1 | 11/2002 | Bonda et al. .................. 424/59 |
| 6,491,901 B2 | 12/2002 | Gers-Barlag et al. ......... 424/59 |
| 6,544,305 B2 | 4/2003 | Wood et al. .................. 44/275 |
| 6,610,409 B2 | 8/2003 | Pickett et al. ............ 428/423.7 |
| 6,689,474 B2 | 2/2004 | Pickett et al. ............ 428/423.7 |
| 2001/0022966 A1 | 9/2001 | Gers-barlag et al. .......... 424/59 |
| 2002/0194777 A1 | 12/2002 | Wood et al. .................. 44/275 |
| 2003/0000130 A1 | 1/2003 | Wood et al. .................. 44/275 |
| 2003/0069338 A1 | 4/2003 | Goossens et al. ........... 524/186 |
| 2003/0072945 A1 | 4/2003 | Pickett et al. ............... 428/412 |
| 2003/0130390 A1 | 7/2003 | Gorny et al. ............... 524/307 |
| 2003/0180542 A1 | 9/2003 | Pickett et al. ............ 428/423.7 |
| 2004/0057912 A1 | 3/2004 | Bonda et al. .................. 424/59 |

OTHER PUBLICATIONS

Haslem, "Recent Developments in Methods For the Esterification and Protection of the Carboxyl Group," *Tetrahedron*, vol. 36, pp. 2409–2433 (1980).

Kamlet et al., "An Examination of Linear Solvation Energy Relationships," *Progr. Phys. Org. Chem.*, vol. 13, pp. 485–630 (1981).

Kosower, "The Effect of Solvent on Spectra. I. A New Empirical Measure of Solvent Polarity Z–Values," *J. Am Chem. Soc.*, vol. 80, pp. 3253–3260 (1958).

McNaught et al., "IUPAC Compendium of Chemical Terminology," $2^{nd}$ Ed. (1997).

Reichardt, "Solvents and Solvent Effects in Organic Chemistry," 2nd Ed., Chap. 7: Empirical Parameters of Solvent Polarity, VCH Publishers, New York, New York (1998).

Sayre et al., "Photostability Testing of Avobenzone," Allured's Cosmetics & Toiletries Magazine, vol. 114, No. 5, pp. 85–91 (May 1999).

Tarras–Wahlberg et al., "Changes in Ultraviolet Absorption of Sunscreens After Ultraviolet Radiation," *J. Investigative Dermatology*, vol. 113, No. 4, pp. 547–553 (1999).

Turro, *Modern Molecular Photochemistry* Benjamin/Cummings Publ. Co., Menlo Park, California, pp. 296–361 (1991).

* cited by examiner

PHOTOSTABILIZERS, UV ABSORBERS, AND METHODS OF PHOTOSTABILIZING A SUNSCREEN COMPOSITION

CROSS-REFERENCE TO RELATED APPLICATIONS

This is a continuation-in-part of U.S. patent application Ser. No. 10/246,434, filed Sep. 17, 2002.

BACKGROUND OF THE INVENTION

Field of the Invention

The invention relates to compounds and methods to increase the photostability of a sunscreen composition. Moreover, the invention relates to photostable sunscreen compositions and a new class of photoactive compounds. More particularly, the invention relates to the use of derivatives of diphenylmethylenemalonic acid and derivatives of fluorene, including derivatives of cyano(9H-fluoren-9-ylidene) acetic acid and diesters and polyesters of 9H-fluoren-9-ylidenemalonic acid to photostabilize a sunscreen composition.

Brief Description of Related Technology

It is well known that ultraviolet radiation (light) having a wavelength from about 280 nm or 290 nm to about 320 nm (UV-B) is harmful to human skin, causing burns that are detrimental to the development of a good sun tan. UV-A radiation (about 320 nm to about 400 nm), while producing tanning of the skin, also can cause damage, particularly to very lightly-colored or sensitive skin, leading to reduction of skin elasticity and wrinkles. Therefore, a sunscreen composition for use on human skin preferably includes both a UV-A and a UV-B filter to prevent most of the sunlight within the full range of about 280 nm or 290 nm to about 400 nm from damaging human skin.

Ultraviolet radiation from the sun or artificial sources can also cause harm to coatings containing photoactive substances, such as photoactive pigments and dyes, by breaking down chemical bonds in the structure of a component such as a polymer, a pigment, or a dye. This photodegradation can lead to color fading, loss of gloss, and loss of physical and protective properties of a coating. Photodegradation can take place in several steps which include one or more components of a coating absorbing UV radiation. The absorbed radiation can excite the absorbing molecules and raise them to a higher energy level, which can be very reactive. If the molecule cannot be relaxed, bond cleavage and the formation of free radicals will occur. These free radicals can attack one or more color molecules and/or a polymer backbone and form more free radicals. UV-A and UV-B filters can also be used to absorb UV radiation to protect a pigmented coating.

The UV-B filters that are most widely used in the U.S. in commercial sunscreen compositions are paramethoxycinnamic acid esters, such as 2-ethylhexyl paramethoxycinnamate, commonly referred to as octyl methoxycinnamate or PARSOL MCX, octyl salicylate, and oxybenzone.

The organic UV-A filters most commonly used in commercial sunscreen compositions are the dibenzoylmethane derivatives, particularly 4-(1,1-dimethylethyl)-4'-methoxydibenzoylmethane (also called avobenzone, sold under the brand name PARSOL 1789). Other dibenzoylmethane derivatives described as UV-A filters are disclosed in U.S. Pat. Nos. 4,489,057, 4,387,089 and 4,562,067, the disclosures of which are hereby incorporated herein by reference. It is also well known that the above described UV-A filters, particularly the dibenzoylmethane derivatives, can suffer from rapid photochemical degradation, when used alone or when combined with the above-described most commercially used UV-B filters.

Typically, the above-described UV-B filters are combined with the above described UV-A filters in a solution with other lipophilic or oily ingredients. This solution of oily ingredients, known to formulators of cosmetic products including sunscreens as the "oil phase," is typically, but not necessarily, dispersed with the help of emulsifiers and stabilizers into an aqueous solution composed primarily of water, to make an emulsion which becomes a final cream or lotion form of a sunscreen composition.

The performance of a photoactive compound or a combination of photoactive compounds in a sunscreen composition has been extremely difficult to predict based on the levels of photoactive compounds in the formulation, particularly when the formulation includes one or more photoactive compounds that suffer from relatively rapid photodegradation, such as avobenzone. Because of this, each formulation has required expensive laboratory testing to determine the UV absorbance, as a function of time (quantity) of exposure of the formulation to UV radiation. Moreover, a particularly difficult problem is presented when one photoactive compound in a sunscreen composition acts to increase the rate of photodegradation of another photoactive compound in the composition. This can be accomplished in a number or ways, including a bimolecular reaction between two photoactive compounds and a lowering of the threshold energy need to raise a photoactive compound to its excited state. For example, when avobenzone is combined with octyl methoxycinnamate a bimolecular pathway leads to the rapid photodegradation of both the dibenzoylmethane derivative and the octyl methoxycinnamate.

Methods and compositions for stabilizing photoactive compounds, such as dibenzoylmethane derivatives with the use of diesters and/or a polyesters of naphthalene dicarboxylic acid are described in U.S. Pat. Nos. 5,993,789, and 6,284,916, the disclosures of which are hereby incorporated herein by reference. Other methods of stabilizing a dibenzoylmethane derivative include the addition of an α-cyano-β,β-diphenylacrylate compound to a sunscreen composition including a dibenzoylmethane derivative. See, Deflandre et al, U.S. Pat. No. 5,576,354 and Gonzenbach et al., U.S. Pat. No. 6,033,649.

SUMMARY

Figure 1:
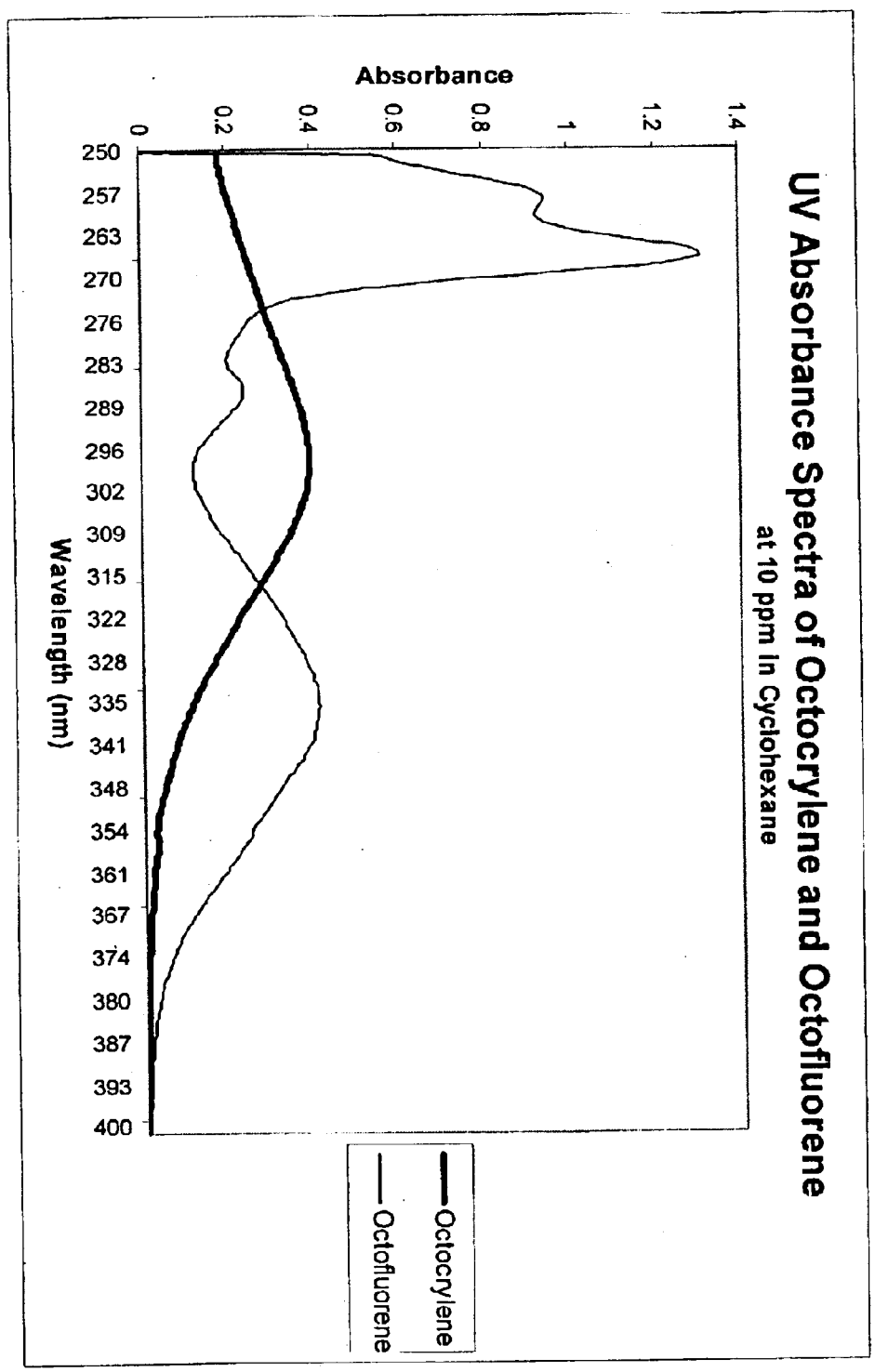
FIG. 1 is a graph of the absorbance of octocrylene (2-ethylhexyl-2-cyano-3,3 diphenylacrylate) and octofluorene (2-ethylhexyl cyano(9H-fluoren-9-ylidene) acetate) from a wavelength of 250 nm to 400 nm, and at a concentration of 10 ppm (parts per million) in cyclohexane.
Figure 2:
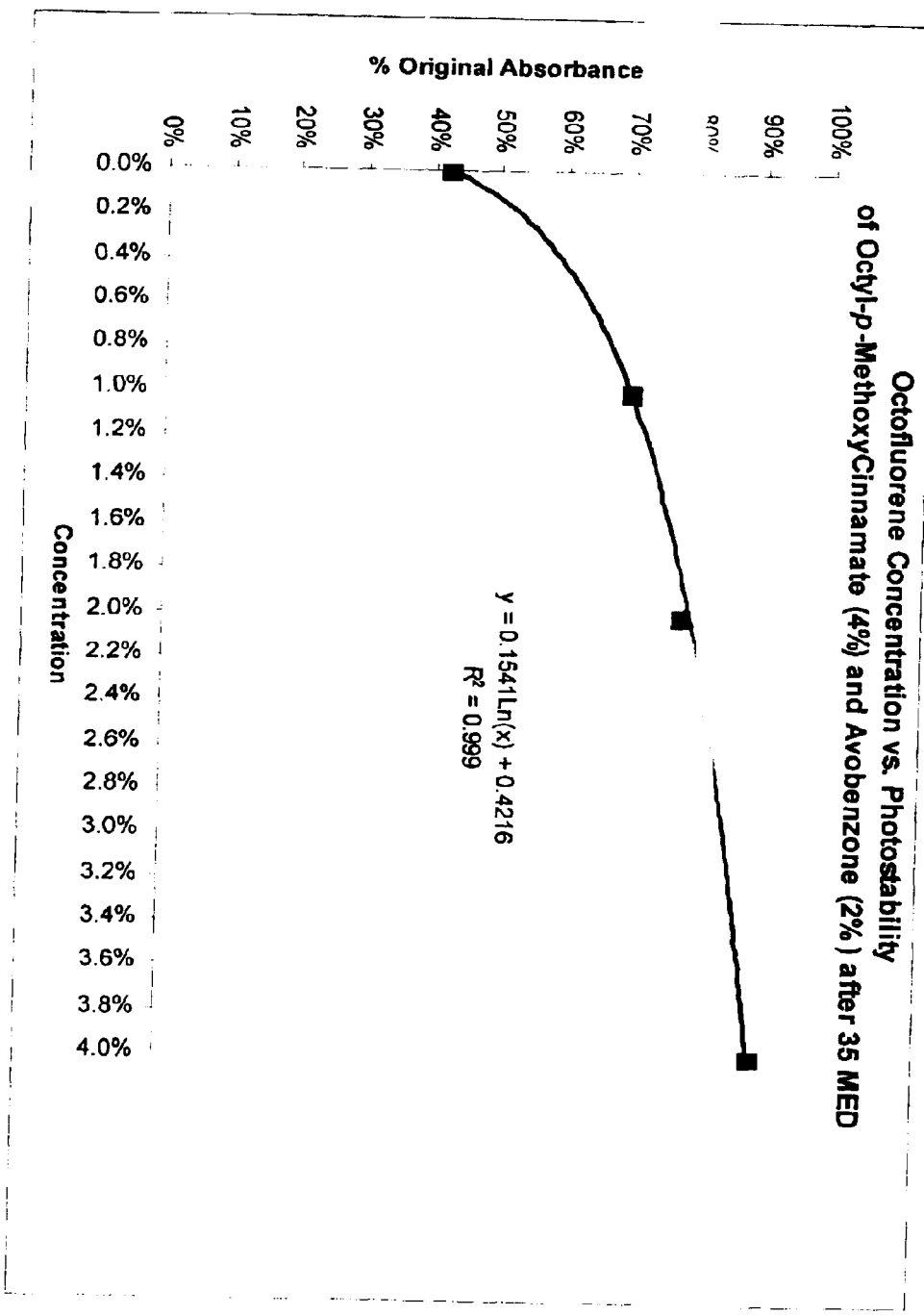
FIG. 2 is a graph of the percent of the original absorbance of sunscreen compositions including 4% by weight of octyl-p-methoxycinnamate and 2% by weight of avobenzone at a wavelength of 370 nm, at various concentrations of octofluorene after the compositions have been exposed to 35 minimal erythemal dose (MED)units, wherein 1 MED is 21 millijoules per square centimeter (mJ/cm2).

One aspect of the invention is a composition including a mixture of a photoactive compound and a compound selected from the group of compounds including derivatives of diphenylmethylenemalonic acid and derivatives of fluorene (e.g., derivatives of cyano(9H-fluoren-9-ylidene) acetic acid, and diesters and polyesters of 9H-fluoren-9-ylidenemalonic acid).

Another aspect of the invention includes derivatives of cyano(9H-fluoren-9-ylidene) acetic acid.

Still another aspect of the invention is a diester and/or a polyester of diphenylmethylenemalonic acid.

Yet another aspect of the invention is a method for stabilizing a sunscreen composition including a photoactive compound by the addition of a derivative of 9-methylene-9H-fluorene.

Still another aspect of the invention is a method for stabilizing a sunscreen composition including a photoactive compound by the addition of a diester or a polyester of diphenylmethylenemalonic acid.

Still another aspect of the invention is method of filtering out ultra-violet light by the use of a derivative of 9-methylene-9H-fluorene.

DETAILED DESCRIPTION OF THE PREFERRED EMBODIMENTS

Sunscreen compositions containing one or more of a photoactive compound, such as a dibenzoylmethane derivative UV-A filter compound, and a derivative of 9-methylene-9H-fluorene and/or diesters of diphenylmethylene malonic acid are described herein. One aspect of the sunscreen compositions described herein are methods of photostabilizing a sunscreen composition including a dibenzoylmethane derivative, such as 4-(1,1-dimethylethyl)-4'-methoxydibenzoylmethane (PARSOL® 1789), wherein one or more photoactive compounds present in a sunscreen composition (e.g., avobenzone) are made more photostable by the addition of a derivative of diphenylmethylenemalonic acid and/or a derivative of fluorene, including a derivative of cyano(9H-fluoren-9-ylidene) acetic acid and diesters and polyesters of 9H-fluoren-9-ylidenemalonic acid. Also disclosed herein are methods for filtering out ultra-violet light from human skin including the step of applying a derivative of cyano(9H-fluoren-9-ylidene) acetic acid to the skin.

A photoactive compound can be considered stable when, for example, after 30 MED irradiation the photoactive compound has retained at least about 90% of its original absorbance at a wavelength or a range of wavelengths of interest (e.g., the wavelength at which or near a photoactive compound has a peak absorbance, such as 350–370 nm for avobenzone). Likewise, a sunscreen composition can include a plurality of photoactive compounds and a sunscreen composition, as a whole, can be considered stable when, for example, after 30 MED irradiation the sunscreen composition has retained at least about 90% of its original absorbance at one or more wavelengths of interest (e.g., at or near the peak absorbance wavelength of the primary photoactive compounds).

It has surprisingly been found that the addition of one or more of a derivative of diphenylmethylenemalonic acid and a derivative of fluorene (including a derivative of cyano(9H-fluoren-9-ylidene) acetic acid and diesters and polyesters of 9H-fluoren-9-ylidenemalonic acid) to a sunscreen composition including a diester or polyester of naphthalene dicarboxylic acid can significantly increase the photostability of the sunscreen composition and/or photounstable components present therein. Without intending to be limited to any particular mechanism of achieving this increase in stability, it is believed that a diester or polyester of naphthalene dicarboxylic acid stabilizes a dibenzoylmethane derivative by accepting the triplet energy of the dibenzoylmethane derivative once the dibenzoylmethane derivative has reached an excited state as a result of the absorption of ultra-violet light. Once a dibenzoylmethane derivative is excited, it is prone to degrade according to a number of pathways; however, the degradation of the dibenzoylmethane derivative can be substantially reduced or prevented by the use of a diester or polyester of naphthalene dicarboxylic acid to quench (accept) the triplet excited state energy present in an excited dibenzoylmethane molecule. Thus, in one pathway of degradation, a dibenzoylmethane derivative is excited to its triplet state and the excited state triplet energy is released in a bond breaking step, thereby preventing the dibenzoylmethane derivative from further accepting ultra-violet radiation. A diester or polyester of naphthalene dicarboxylic acid may stabilize a dibenzoylmethane derivative by accepting the triplet state (excited state) energy of the excited dibenzoylmethane derivative in such a way as to convert the excited dibenzoylmethane derivative back to a ground state that is capable of reaccepting ultra-violet radiation (energy transfer).

For this process to work continuously, the diester or polyester of naphthalene dicarboxylic acid must transfer or convert the energy that was accepted from the excited dibenzoylmethane derivative. Without intending to be limited to a particular mechanism, it is believed that when a diester or polyester of naphthalene dicarboxylic acid is excited to its triplet state it dissipates the triplet excited state energy through vibrations (e.g., as heat), which in this group of molecules is a relatively slow mode of dissipating energy. It has been found, quite surprisingly, that by the addition of even low levels (e.g., less than 1% by weight) or very low levels (e.g., 0.5% by weight or less) of a derivative of fluorene (e.g., a derivative of cyano(9H-fluoren-9-ylidene) acetic acid and a diester and/or a polyester of 9H-fluoren-9-ylidenemalonic acid), such a compound is able to accept triplet excited state energy from an excited diester or polyester of naphthalene dicarboxylic acid. Thus, according to one possible mechanism, the efficiency of the dissipation of the excited state energy in an excited diester or polyester of naphthalene dicarboxylic acid is greatly improved by a transfer of energy from an excited diester or polyester of naphthalene dicarboxylic acid to a derivative of fluorene (e.g., a derivative of cyano(9H-fluoren-9-ylidene) acetic acid and a diester and/or a polyester of 9H-fluoren-9-ylidenemalonic acid).

Thus, preferably, a sunscreen composition disclosed herein includes a diester or polyester of naphthalene dicarboxylic acid selected from the group consisting of compounds of formulae (VII) and (VIII), and combinations thereof:

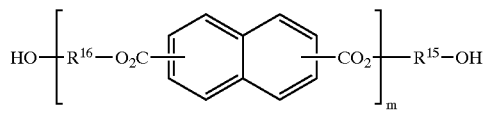

(VII)

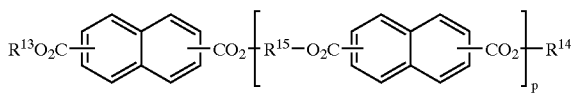

(VIII)

wherein $R^{13}$ and $R^{14}$ are the same or different and are selected from the group consisting of $C_1$–$C_{22}$ alkyl groups, diols having the structure HO—$R^{15}$—OH, and polyglycols having the structure HO—$R^{16}$—(—O—$R^{15}$—)$_n$—OH; wherein each $R^{15}$ and $R^{16}$ is the same or different and selected from the group consisting of $C_1$–$C_6$ straight or branched chain alkyl groups; and wherein m and n are each in a range of 1 to 100 and p is in a range of 0 to 100. Preferably, a sunscreen composition includes a diester of formula (VIII) wherein $R^1$ and $R^2$ are 2-ethylhexane and p is 0.

A sunscreen composition disclosed herein can be combined into a cosmetically acceptable carrier, optionally including emollients, stabilizers, emulsifiers, such as those known in the art, and combinations thereof. These additives can be used in preparing an emulsion from an aqueous system and a mixture of a filter system that includes one or more photoactive compounds and a solvent system that includes one or more organic solvents. When made, preferably the emulsion is an oil-in-water emulsion, wherein the oil phase is primarily formed from a mixture of the filter system and solvent system.

A typical sunscreen composition includes one or more photoactive compounds, wherein a photoactive compound acts to absorb UV radiation and thereby protect the substrate (e.g., human skin) from the harmful effects of UV radiation. The absorption process causes a photoactive compound to reach an excited state, wherein the excited state is characterized by the presence of excited energy (e.g., singlet energy or triplet energy), as compared to the ground state of the photoactive compound. Once a photoactive compound reaches an excited state there exists a number of pathways by which the excited photoactive compound can dissipate its excess energy (e.g., triplet energy), however, many of those pathways adversely affect the ability of the photoactive compound to further absorb UV radiation.

It has surprisingly been found that the addition of one or more of a derivative of diphenylmethylenemalonic acid and a derivative of fluorene (including derivative of cyano(9H-fluoren-9-ylidene) acetic acid and diesters and polyesters of 9H-fluoren-9-ylidenemalonic acid) increases the photostability of a sunscreen composition. Without intending to be limited to any particular mechanism by which a such compounds are able to quench (accept the excited state energy) an excited photoactive compound, it is believed that, for example a 9-methylene-9H-fluorene derivative accepts the excited state energy and dissipates the energy kinetically in the form of rapid isomerizations. An example of this process is shown below:

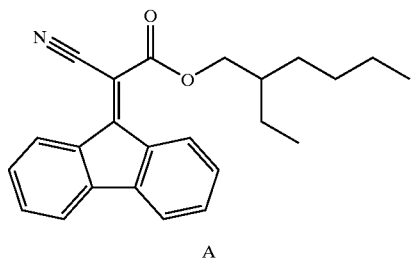 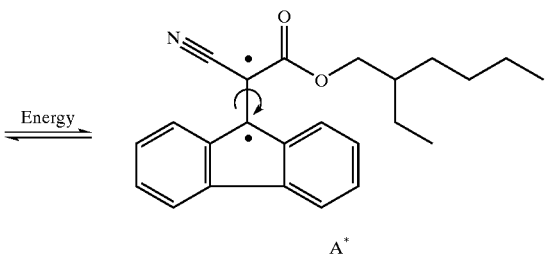

A                        A* wherein the 9-methylene-9H-fluorene derivative (2-ethylhexyl cyano(9H-fluoren-9-ylidene) acetate, shown above as A and hereinafter referred to as octofluorene), accepts the triplet excited state energy and forms a diradical (shown above as A*) at the α and β positions of the acrylate, which converts the double bond into a single bond and allows for free rotation about the single bond. This rotation occurs rapidly and efficiently to dissipate excited state energy accepted by a derivative of fluorene.

Commonly-assigned U.S. patent application Ser. Nos. 10/092,131, now U.S. Pat. No. 6,537,529, and Ser. No. 10/092,132, now U.S. Pat. No. 6,485,713, the disclosures of which are hereby incorporated herein by reference, describe compositions and methods for increasing the stability of photoactive compounds in a sunscreen composition, e.g., by the addition of polar solvents to the oil phase of a composition. It has been found, quite surprisingly, that by increasing the polarity of the oil phase of a sunscreen composition including one or more of a derivative of diphenylmethylenemalonic acid and a derivative of fluorene, the stability of the sunscreen composition is increased. Now knowing that the polarity of the solution affects the stability, one might expect that the more polar the solution is, the greater the stability it will impart to the photoactive compound. In contrast, and even more surprisingly, it has been found that as the polarity of a solvent system including a dissolved, rapidly photodegradable compound is increased, the rate of photodecay initially decreases but then increases again as the polarity is further increased. Thus, a photodegradable compound in solution will degrade as a second-order function of the overall polarity of the solution. Currently accepted photochemical theory provides the possibility that the mechanism by which a photodegradable compound is stabilized is the transfer of a photonically-excited electron to a nearby molecule of the same or different species (see, e.g., N. J. Turro, Modern Molecular Photochemistry, Chapter 9, Benjamin/Cummings Publ. Co., Menlo Park, Calif. (1991)), however photochemical theory does not describe the observed phenomena. Though not intending to be bound by such a belief, the observed phenomena are believed to coincide with the electron transfer theory of Professor Rudolph A. Marcus of the California Institute of Technology, for which he received the 1992 Nobel Prize in Chemistry.

The dielectric constant of a solvent system is a preferred measure of polarity of a solvent system, for example because the dielectric constant is a measure of both inherent and inducible dipole moments. Other measures of polarity include, but are not limited to, the induced and/or inherent (permanent) dipole moment (e.g., in Debye units), the Dimroth-Reichardt $E_T$ parameter, and ionizing power. See generally, C. Reichardt, "Solvents and Solvent Effects in Organic Chemistry" 2nd ed., Chap. 7: Empirical Parameters of Solvent Polarity, VCH Publishers, New York, N.Y, (1988). Moreover, a more detailed description of these methods of measuring the polarity of the compound or a series of compounds can be found in commonly assigned U.S. patent application Ser. Nos. 10/092,131 and 10/092,132.

Mathematically, photodegradation can be described by an exponential function. Thus, Q(a), the absorbance after a radiation dose (i.e., exposure to a quantity of radiation), can be described by the general equation (i), $$Q(a) = A e^{-kr} \quad (i)$$

wherein A is the original (pre-exposure) absorbance, e is the natural logarithm base, k is the rate constant of the photodecay, and r is the cumulative dose (e.g., in MED units). Because the absorbance decreases as the cumulative dose increases (photodecay), the overall term −k will be negative, and the greater the value of −k (i.e., closer to zero) and, thus, the lower the rate constant of photodecay, the lower is the rate of photodecay. For example, when Q(a) is plotted on a log scale versus r on a linear scale, the function forms a straight line with a slope equal to −k.

Furthermore, it has been found that, for a set of photoactive compounds that includes a photodegradable compound (e.g. avobenzone), the rate constant of photodecay of the set of photoactive compounds can be described as a second-order function of the polarity, preferably the dielectric constant (i.e., relative permittivity) of the filter set dissolved in the solvent system. Thus, for example, the rate constant of photodecay of a filter set that include one or more of a photoactive compound, can be described by the general equation (ii), $$k = -(x\epsilon^2 + y\epsilon + z) \quad (ii)$$

wherein x, y, and z can be empirically determined. The dielectric constant at the theoretical minimum rate constant of photodecay −k min described by formula (iii), $$\epsilon_{k\,min} = \frac{-y}{2x} \quad (iii)$$

wherein x and y are defined as above.

The phenomena described above, coupled with the knowledge that, heretofore, sunscreen compositions have been formulated without specific regard to. the relationship between polarity and photostability and, in newly-discovered fact, have had non-optimal polarities, forms the basis for at least one aspect of the compositions and methods described herein.

In a sunscreen disclosed herein, preferably, one or more of a highly polar solvent is present in the oil-phase of the composition. Preferably, a sufficient amount of a polar solvent is present in a sunscreen composition to raise the dielectric constant of the oil-phase of the composition to a dielectric constant of at least about 7, preferably at least about 8.

A photoactive compound is one that responds to light photoelectrically. In the compositions disclosed herein, a photoactive compound is one that responds to UV radiation photoelectrically. For example, photoactive compounds that respond to UV radiation photoelectrically by rapid photodegradation can benefit highly from the compositions and methods disclosed herein, even though the benefits of the compositions and methods disclosed herein are not limited to such compounds. Photostability is a potential problem with all UV filters because they are deliberately selected as UV-absorbing molecules. In other applications, a photoactive compound may be a pigment or a dye (e.g., a hydrophobic dye).

UV filters include compounds selected from the following categories (with specific examples) including: p-aminobenzoic acid, its salts and its derivatives (ethyl, isobutyl, glyceryl esters; p-dimethylaminobenzoic acid); anthranilates (o-aminobenzoates; methyl, menthyl, phenyl, benzyl, phenylethyl, linalyl, terpinyl, and cyclohexenyl esters); salicylates (octyl, amyl, phenyl, benzyl, menthyl (homosalate), glyceryl, and dipropyleneglycol esters); cinnamic acid derivatives (menthyl and benzyl esters, alpha-phenyl cinnamonitrile; butyl cinnamoyl pyruvate); dihydroxycinnamic acid derivatives (umbelliferone, methylumbelliferone, methylaceto-umbelliferone); camphor derivatives (3-benzylidene, 4-methylbenzylidene, polyacrylamidomethyl benzylidene, benzalkonium methosulfate, benzylidene camphor sulfonic acid, and terephthalylidene dicamphor sulfonic acid); trihydroxycinnamic acid derivatives (esculetin, methylesculetin, daphnetin, and the glucosides, esculin and daphnin); hydrocarbons (diphenylbutadiene, stilbene); dibenzalacetone; benzalacetophenone; naphtholsulfonates (sodium salts of 2-naphthol-3,6-disulfonic and of 2-naphthol-6,8-disulfonic acids); dihydroxy-naphthoic acid and its salts; o- and p-hydroxydiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric acid derivatives; vilouric acid derivatives; tannic acid and its derivatives; hydroquinone; and benzophenones (oxybenzone, sulisobenzone, dioxybenzone, benzoresorcinol, 2,2',4,4'-tetrahydroxybenzophenone, 2,2'-dihydroxy-4,4'-dimethoxybenzophenone, octabenzone, 4-isopropyldibenzoylmethane, butylmethoxydibenzoylmethane, etocrylene, and 4-isopropyl-dibenzoylmethane).

Particularly useful are: 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl 4-[bis(hydroxypropyl)]aminobenzoate, 2-ethylhexyl-2-cyano-3,3-diphenylacrylate, 2-ethylhexylsalicylate, glycerol p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl-5-sulfoniobenzoxazoic acid, and combinations thereof.

For a product marketed in the United States, preferred cosmetically-acceptable photoactive compounds and concentrations (reported as a percentage by weight of the total cosmetic sunscreen composition) include: aminobenzoic acid (also called para-aminobenzoic acid and PABA; 15% or less), avobenzone (also called butyl methoxy dibenzoylmethane; 3% or less), cinoxate (also called 2-ethoxyethyl p-methoxycinnamate; 3% or less), dioxybenzone (also called benzophenone-8; 3% or less), homosalate (15% or less), menthyl anthranilate (also called menthyl 2-aminobenzoate; 5% or less), octocrylene (also called 2-ethylhexyl-2-cyano-3,3 diphenylacrylate; 10% or less), octyl methoxycinnamate (7.5% or less), octyl salicylate (also called 2-ethylhexyl salicylate; 5% or less), oxybenzone (also called benzophenone-3; 6% or less), padimate O (also called octyl dimethyl PABA; 8% or less), phenylbenzimidazole sulfonic acid (water soluble; 4% or less), sulisobenzone (also called benzophenone-4; 10% or less), titanium dioxide (25% or less), trolamine salicylate (also called triethanolamine salicylate; 12% or less), and zinc oxide (25% or less).

Other preferred cosmetically-acceptable photoactive compounds and preferred concentrations (percent by weight of the total cosmetic sunscreen composition) include diethanolamine methoxycinnamate (10% or less), ethyl-[bis(hydroxypropyl)]aminobenzoate (5% or less), glyceryl aminobenzoate (3% or less), 4-isopropyl dibenzoylmethane (5% or less), 4-methylbenzylidene camphor (6% or less), terephthalylidene dicamphor sulfonic acid (10% or less), and sulisobenzone (also called benzophenone-4, 10% or less).

For a product marketed in the European Union, preferred cosmetically-acceptable photoactive compounds and preferred concentrations (reported as a percentage by weight of the total cosmetic sunscreen composition) include: PABA (5% or less), camphor benzalkonium methosulfate (6% or less), homosalate (10% or less), benzophenone-3 (10% or less), phenylbenzimidazole sulfonic acid (8% or less, expressed as acid), terephthalidene dicamphor sulfonic acid (10% or less, expressed as acid), butyl methoxydibenzoylmethane (5% or less), benzylidene camphor sulfonic acid (6% or less, expressed as acid), octocrylene (10% or less, expressed as acid), polyacrylamidomethyl benzylidene camphor (6% or less), ethylhexyl methoxycinnamate (10% or less), PEG-25 PABA (10% or less), isoamyl p-methoxycinnamate (10% or less), ethylhexyl triazone (5% or less), drometrizole trielloxane (15% or less), diethylhexyl butamido triazone (10% or less), 4-methylbenzylidene camphor (4% or less), 3-benzylidene camphor (2% or less), ethylhexyl salicylate (5% or less), ethylhexyl dimethyl PABA (8% or less), benzophenone-4 (5%, expressed as acid), methylene bis-benztriazolyl tetramethylbutylphenol (10% or less), disodium phenyl dibenzimidazole tetrasulfonate (10% or less, expressed as acid), bis-ethylhexyloxyphenol methoxyphenol triazine (10% or less), methylene bisbenzotriazolyl tetramethylbutylphenol (10% or less, also called TINOSORB M), and bisethylhexyloxyphenol methoxyphenyl triazine.(10% or less, also called TINOSORB S).

All of the above-described UV filters are commercially available. For example, suitable commercially-available organic UV filters are identified by trade name and supplier in Table I below:

TABLE I

| CTFA Name | Trade Name | Supplier |
|---|---|---|
| benzophenone-3 | UVINULM-40 | BASF Chemical Co. |
| benzophenone-4 | UVINUL MS-40 | BASF Chemical Co. |
| benzophenone-8 | SPECTRA-SORB UV-24 | American Cyanamid |
| DEA-methoxycinnamate | BERNEL HYDRO | Bernel Chemical |
| ethyl dihydroxypropyl-PABA | AMERSCREEN P | Amerchol Corp. |
| glyceryl PABA | NIPA G.M.P.A. | Nipa Labs. |
| homosalate | KEMESTER HMS | Humko Chemical |
| methyl anthranilate | SUNAROME UVA | Felton Worldwide |
| octocrylene | UVINUL N-539 | BASF Chemical Co. |
| octyl dimethyl PABA | AMERSCOL | Amerchol Corp. |
| octyl methoxycinnamate | PARSOL MCX | Bernel Chemical |
| PABA | PABA | National Starch |
| 2-phenylbenzimidazole-5-sulphonic acid | EUSOLEX 6300 | EM Industries |
| TEA salicylate | SUNAROME W | Felton Worldwide |
| 2-(4-methylbenzildene)-camphor | EUSOLEX 6300 | EM Industries |
| benzophenone-1 | UVINUL 400 | BASF Chemical Co. |
| benzophenone-2 | UVINUL D-50 | BASF Chemical Co. |
| benzophenone-6 | UVINUL D-49 | BASF Chemical Co. |
| benzophenone-12 | UVINUL 408 | BASF Chemical Co. |
| 4-isopropyl dibenzoyl methane | EUSOLEX 8020 | EM Industries |
| butyl methoxy dibenzoyl methane | PARSOL 1789 | Givaudan Corp. |
| etocrylene | UVINUL N-35 | BASF Chemical Co. |
| methylene bisbenzotriazolyl tetramethylbutylphenol | TINOSORB M | Ciba Specialty Chemicals |
| bisethylhexyloxyphenol methoxyphenyl triazine. | TINOSORB S | Ciba Specialty Chemicals |

The term "alkyl" as used herein refers to straight- and branched-chain hydrocarbon groups, preferably containing one to thirty carbon atoms. Examples of alkyl groups are $C_1$–$C_4$ alkyl groups. As used herein the designation $C_x$–$C_y$, wherein x and y are integers, denotes a group having from x to y carbon atoms, e.g., a $C_1$–$C_4$ alkyl group is an alkyl group having one to four carbon atoms. The term alkyl also includes variations of an alkyl group including, an alkene (containing a double bond) and an alkyene group (containing a triple bond). Nonlimiting examples of alkyl groups include, methyl, ethyl, n-propyl, isopropyl, n-butyl, sec-butyl (2-methylpropyl), and t-butyl (1,1-dimethylethyl).

The term "hydroxy" as used herein refers to an "—OH" group.

The term "cycloalkyl" as used herein refers to an aliphatic cyclic hydrocarbon group, preferably containing three to eight carbon atoms. Nonlimiting examples of cycloalkyl groups include cyclopropyl, cyclobutyl, cyclopentyl, and cyclohexyl.

The terms "substituted alkyl" and "substituted cycloalkyl" as used herein refer to an alkyl or cycloalkyl groups having one or more substituents. The substituents can include, but are not limited to, one or more of $C_3$–$C_8$ cycloalkyl, hydroxyalkyl, substituted cycloalkyl, ester, ether, aryl, heteroaryl, heterocycloalkyl, substituted aryl, substituted heteroaryl, substituted heterocycloalkyl, hydroxyl, halogen, cyano, amide, imide, urethane, and amino. The preferred substituted alkyl groups have one to twenty carbon atoms, not including carbon atoms of the substituent group. Preferably, a substituted alkyl group is mono- or di-substituted at one, two, or three carbon atoms. The substituents can be bound to the same carbon or different carbon atoms.

The term "ester" as used herein refers to a group of the general formula:

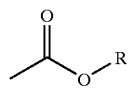

wherein R is an alkyl group, cycloalkyl group, substituted alkyl group, or a substituted cycloalkyl group.

The term "amide" as used herein refers to a group of the general formula:

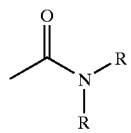

wherein R is a hydrogen, alkyl group, cycloalkyl group, substituted alkyl group, or a substituted cycloalkyl group.

The term "imide" as used herein refers to a group of the general formula:

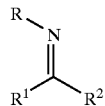

wherein R, $R^1$, and $R^2$ are each independently selected from alkyl groups, cycloalkyl groups, substituted alkyl groups, and substituted cycloalkyl groups.

The term "urethane" as used herein refers to a group of the general formula:

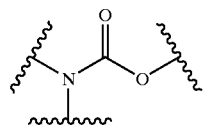

The term "aryl" as used herein refers to monocyclic, fused bicyclic, and fused tricyclic carbocyclic aromatic ring systems including, but not limited to, phenyl, naphthyl, tetrahydronaphthyl, phenanthrenyl, biphenylenyl, indanyl, indenyl, anthracenyl, and fluorenyl.

The term "heteroaryl" as used herein refers to monocyclic, fused bicyclic, and fused tricyclic aromatic ring systems, wherein one to four-ring atoms are selected from the group consisting of oxygen, nitrogen, and sulfur, and the remaining ring atoms are carbon, said ring system being joined to the remainder of the molecule by any of the ring atoms. Nonlimiting examples of heteroaryl groups include, but are not limited to, pyridyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, furanyl, quinolinyl, isoquinolinyl, benzoxazolyl, benzimidazolyl, and benzothiazolyl.

The term "heterocycloalkyl" as used herein refers to an aliphatic, partially unsaturated or fully saturated, 2- to 14-membered ring system, including single rings of 3 to 8 atoms and bi- and tricyclic ring systems. The heterocycloalkyl ring systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, triazine, benzotriazine, piperidinyl, piperazinyl, oxazolidinyl, isoxazolidinyl, morpholinyl, thiazolidinyl, isothiazolidinyl, and tetrahydrofuryl.

The terms "substituted aryl," "substituted heteroaryl," and "substituted heterocycloalkyl" as used herein refer to an aryl, heteroaryl, or heterocycloalkyl group substituted by a replacement of one, two, or three of the hydrogen atoms thereon with a substitute selected from the group consisting of $C_3$–$C_8$ cycloalkyl, hydroxyalkyl, substituted cycloalkyl, ester, ether, aryl, heteroaryl, heterocycloalkyl, substituted aryl, substituted heteroaryl, substituted heterocycloalkyl, hydroxyl, halogen, cyano, amino, amide, imide, urethane, OR, $N(R)_2$, $C(=O)N(R)_2$, $O(CH_2)_{1-3}N(R)_2$, $O(CH_2)_{1-3}CO_2H$, and trifluoromethyl.

The term "amino" as used herein refers an —$NH_2$ or —NH— group, wherein each hydrogen in each formula can be replaced with an alkyl, cycloalkyl, aryl, heteroaryl, heterocycloalkyl, substituted alkyl, substituted cycloalkyl, substituted aryl, substituted heteroaryl, or substituted heterocycloalkyl group, i.e., $N(R)_2$. In the case of —$NH_2$, the hydrogen atoms also can be replaced with substituents taken together to form a 5- or 6-membered aromatic or non-aromatic ring, wherein one or two carbons of the ring optionally are replaced with a heteroatom selected from the group consisting of sulfur, oxygen, and nitrogen. The ring also optionally can be substituted with an alkyl group. Examples of rings formed by substituents taken together with the nitrogen atom include morpholinyl, phenylpiperazinyl, imidazolyl, pyrrolidinyl, (N-methyl) piperazinyl, and piperidinyl.

The term "hydroxyalkyl" as used herein refers to one or more of a hydroxy group attached as a substituent to a $C_1$–$C_{30}$ alkyl group.

The term "substituted hydroxyalkyl" as used herein refers to an hydroxyalkyl group that is substituted with one or more of $C_3$–$C_8$ cycloalkyl, hydroxyalkyl, substituted cycloalkyl, ester, ether, aryl, heteroaryl, heterocycloalkyl, substituted aryl, substituted heteroaryl, substituted heterocycloalkyl, alkoxy, halogen, cyano, amide, imide, urethane, and amino.

The term "ether" as used herein refers to a $C_1$–$C_{50}$ alkyl group that includes one or more of an oxygen atom inserted within the alkyl group. For example, a diethyl ether (—$CH_2CH_2CH_2CH_3$) substituent is a $C_4$ ether.

The term "substituted ether" as used herein refers to an ether group that is substituted with one or more of $C_3$–$C_8$ cycloalkyl, hydroxyalkyl, substituted cycloalkyl, ester, ether, aryl, heteroaryl, heterocycloalkyl, substituted aryl, substituted heteroaryl, substituted heterocycloalkyl, hydroxyl, halogen, cyano, amide, imide, urethane, and amino. For example, 1-ethoxyethanol (—CH$_2$CH$_2$OCH (OH)CH$_3$) is a C$_4$ substituted ether, wherein a hydroxyl group is a substituent on the ether.

The term "polyalkylglycol" as used herein refers to compounds of the general structure of R$^1$(OR)$_n$OH, wherein R is selected from C$_1$–C$_{30}$ alkyl groups and C$_1$–C$_{30}$ substituted alkyl groups, and R$^1$ is selected from hydrogen, C$_1$–C$_{30}$ alkyl groups, C$_1$–C$_{30}$ substituted alkyl groups, C$_3$–C$_8$ cycloalkyl, hydroxyalkyl, substituted cycloalkyl, ester, ether, aryl, heteroaryl, heterocycloalkyl, substituted aryl, substituted heteroaryl, substituted heterocycloalkyl, hydroxyl, halogen, cyano, amide, imide, urethane, and amino. For example, polyethylene glycol is a polyalkylglycol wherein R$^1$ is hydrogen and R is a C$_2$ alkyl group. As another example, polypropyleneglycol is a polyalkylglycol wherein R$^1$ is hydrogen and R is a C$_3$ alkyl group.

The term "halogen" as used herein refers to fluorine, chlorine, bromine, and iodine.

The term "cyano" as used herein refers to a —C≡N group, also designated —CN.

A sunscreen composition disclosed herein can include a variety of photoactive compounds, including one or more UV-A photoactive compounds and one or more UV-B photoactive compounds. Preferably, a sunscreen composition includes a photoactive compound selected from the group consisting of p-aminobenzoic acid and salts and derivatives thereof; anthranilate and derivatives thereof; dibenzoylmethane and derivatives thereof; salicylate and derivatives thereof; cinnamic acid and derivatives thereof; dihydroxycinnamic acid and derivatives thereof; camphor and salts and derivatives thereof; trihydroxycinnamic acid and derivatives thereof; dibenzalacetone naphtholsulfonate and salts and derivatives thereof; benzalacetophenone naphtholsulfonate and salts and derivatives thereof; dihydroxynaphthoic acid and salts thereof; o-hydroxydiphenyldisulfonate and salts and derivatives thereof; p-hydroxydiphenyldisulfonate and salts and derivatives thereof; coumarin and derivatives thereof; diazole derivatives; quinine derivatives and salts thereof; quinoline derivatives; hydroxy-substituted benzophenone derivatives; methoxy-substituted benzophenone derivatives; uric acid derivatives; vilouric acid derivatives; tannic acid and derivatives thereof; hydroquinone; benzophenone derivatives; 1,3,5-triazine derivatives, phenyldibenzimidazole tetrasulfonate and salts and derivatives thereof; terephthalylidene dicamphor sulfonic acid and salts and derivatives thereof; methylene bis-benzotriazolyl tetramethylbutylphenol and salts and derivatives thereof; bis-ethylhexyloxyphenol methoxyphenyl triazine and salts and derivatives thereof; diethylamino hydroxybenzoyl hexyl benzoate and salts and derivatives thereof; and combinations of the foregoing.

UV-A radiation (about 320 nm to about 400 nm), is recognized as contributing to causing damage, to skin particularly to very lightly-colored or sensitive skin. A sunscreen composition disclosed herein preferably includes a UV-A photoactive compound. Preferably, a sunscreen composition disclosed herein includes a dibenzoylmethane derivative UV-A photoactive compound. Preferred dibenzoylmethane derivatives include, 2-methyldibenzoylmethane; 4-methyldibenzoylmethane; 4-isopropyldibenzoylmethane; 4-tert-butyldibenzoylmethane; 2,4-dimethyldibenzoylmethane; 2,5-dimethyldibenzoylmethane; 4,4'-diisopropyldibenzoylmethane; 4,4'-dimethoxydibenzoylmethane; 4-tert-butyl-4'-methoxydibenzoylmethane; 2-methyl-5-isopropyl-4'-methoxydibenzoylmethane; 2-methyl-5-tert-butyl-4'-methoxydibenzoylmethane; 2,4-dimethyl-4'-methoxydibenzoylmethane; 2,6-dimethyl-4-tert-butyl-4'-methoxydibenzoylmethane, and combinations thereof.

A preferred combination of photoactive compounds in a sunscreen composition includes a UV-A and a UV-B photoactive compound. However, when 2-ethylhexyl-p-methoxycinnamate is included in a mixture with a dibenzoylmethane derivative, the dibenzoylmethane derivative can become particularly unstable. Without intending to be limited to any particular mechanism, it is believed that the cinnamate ester reacts with an excited-state dibenzoylmethane derivative in a bimolecular pathway that renders both the dibenzoylmethane derivative and the cinnamate ester incapable of absorbing UV radiation. It has been found, quite surprisingly, that the use of one or more of a derivative of diphenylmethylenemalonic acid and derivative of fluorene (including derivatives of cyano(9H-fluoren-9-ylidene) acetic acid and diesters and polyesters of 9H-fluoren-9-ylidenemalonic acid) increases the stability of a sunscreen composition that includes 2-ethylhexyl-p-methoxycinnamate and a dibenzoylmethane derivative. Thus, one embodiment of a sunscreen composition includes 2-ethylhexyl-p-methoxycinnamate, a dibenzoylmethane derivative, and one or more of a derivative of diphenylmethylenemalonic acid and a derivative of fluorene (e.g., derivatives of cyano(9H-fluoren-9-ylidene) acetic acid and diesters and polyesters of 9H-fluoren-9-ylidenemalonic acid). Octofluorene is particularly preferred.

One embodiment of a sunscreen composition disclosed herein includes a mixture of a photoactive compound and a compound selected from the group consisting of compounds of formulae (I), (II), (IV) to (VI), and combinations thereof:

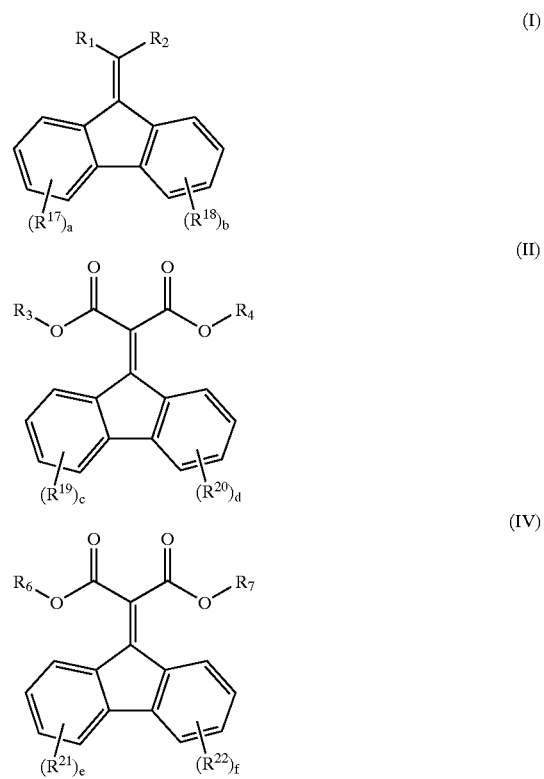

-continued

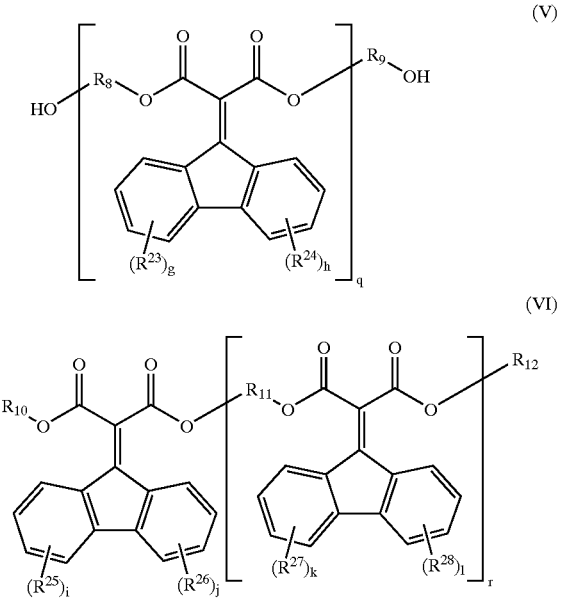

(V)

(VI)

wherein, $R^1$, $R^2$, $R^3$, $R^4$, $R^6$, $R^7$, $R^8$, $R^9$, $R^{10}$, $R^{11}$, and $R^{12}$ are the same or different and are selected from the group consisting of $C_1$–$C_{30}$ alkyl, $C_3$–$C_8$ cycloalkyl, substituted alkyl, hydroxyalkyl, alkoxyalkyl, substituted cycloalkyl, ester, aryl, heteroaryl, heterocycloalkyl, substituted aryl, substituted heteroaryl, substituted heterocycloalkyl, cyano, and amino; $C^{17}$, $C^{18}$, $C^{19}$, $C^{20}$, $C^{21}$, $C^{22}$, $C^{23}$, $C^{24}$, $C^{25}$, $C^{26}$, $C^{27}$, and $C^{28}$ are same or different and are selected from the group consisting of hydrogen, $C_1$–$C_{30}$ alkyl, $C_3$–$C_8$ cycloalkyl, substituted alkyl, hydroxyalkyl, alkoxyalkyl, substituted cycloalkyl, ester, aryl, heteroaryl, heterocycloalkyl, substituted aryl, substituted heteroaryl, substituted heterocycloalkyl, hydroxyl, alkoxy, halogen, cyano, and amino; q and r are each in the range of 0 to 100; and a, b, c, d, e, f, g, h, i, j, and l are each in the range of 0 to 4. Compounds of formula (I), (II), and (IV) to (VI) are able to stabilize one or more photoactive compounds present in a sunscreen composition. Without intending to be limited to any particular mechanism of stabilization, it is believed that the photoactive compounds are stabilized by transferring their excited state energy (e.g., singlet and triplet energy) to a derivative of diphenylmethylenemalonic acid and/or a derivative of fluorene (i.e., a derivative of cyano (9H-fluoren-9-ylidene) acetic acid and a diester and/or polyester of 9H-fluoren-9-ylidenemalonic acid). It is believed that the transfer of excited state energy takes place because it leads to the most efficient dissipation of the excited state energy (e.g., through the rapid isomerizations discussed above). Each of the R groups in a compound of formula (I) or a compound of formula (II) ($R^1$, $R^2$, $R^3$ and $R^4$) is preferably selected from $C_1$–$C_{15}$ branched chain alkyls. Preferably, each of the R groups in a compound of formula (I) or a compound of formula (II) ($R^1$, $R^2$, $R^3$ and $R^4$) is 2-ethylhexane.

It is preferred that a compound selected from the group consisting of compounds of formulae (I), (II), (IV) to (VI), and combinations thereof, is present in a sunscreen composition in a range of about 0.1% to about 25% by weight of the total weight of the composition, more preferably about 0.1% to about 10%, still more preferably about 0.5% to about 5%.

Derivatives of fluorene, including derivatives of cyano (9H-fluoren-9-ylidene) acetic acid and diesters of diphenyl-methylenemalonic acid can be prepared by a Claisen-type (Claisen-Schmidt) condensation reaction. For example, octofluorene can be prepared by reacting 2-ethylhexyl cyanoacetate with 9-fluorenone in the presence of acetic acid and sodium acetate.

Another embodiment of the invention is a compound of formula (III),

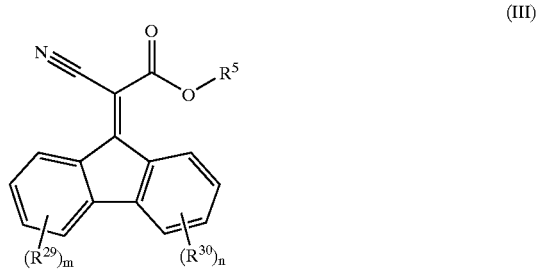

(III)

wherein $R^5$ is selected from the group consisting of $C_3$–$C_{30}$ alkyl, $C_3$–$C_8$ cycloalkyl, substituted alkyl, hydroxyalkyl, substituted hydroxyalkyl, ether, substituted ether, substituted cycloalkyl, aryl, heteroaryl, heterocycloalkyl, substituted aryl, substituted heteroaryl, substituted heterocycloalkyl, and amino; $R^{29}$ and $R^{30}$ are the same or different and are selected from the group consisting of hydrogen, $C_1$–$C_{30}$ alkyl, $C_3$–$C_8$ cycloalkyl, substituted alkyl, hydroxyalkyl, substituted hydroxyalkyl, ether, substituted ether, ester, aryl, heteroaryl, heterocycloalkyl, substituted aryl, substituted heteroaryl, substituted heterocycloalkyl, hydroxyl, alkoxy, halogen, cyano, imide, urethane, amide, and amino; and m and n are each in the range of 0 to 4. Preferably, $R^5$ is selected from $C_3$–$C_{20}$ branched chain alkyls, and $C_1$–$C_{30}$ hydroxyalkyls. More preferably, $R^5$ is a $C_2$–$C_8$ hydroxyalkyl group. In particular, $R^5$ preferably, is selected from the group consisting of ethanol, propan-1-ol, propan-2-ol, 1-buatanol, methylpropan-1-ol, 2,2-dimethylpropan-1-ol, and 2-methylpropan-2-ol.

Compounds of formula (III), quite surprisingly, are able to increase the stability of a photoactive compound in a sunscreen composition. Thus, preferably, a compound of formula (III) is present in a sunscreen composition, for example, in a range of about 0.1% to about 25% by weight of the total weight of the composition, preferably in a range of about 0.1% to about 10%.

Moreover, compounds of formula (III), quite surprisingly, are intensely colored and can be used as a pigment in a paint or other application where it would be advantageous to have a coloring component present in the mixture, and would be expected to be a photostable pigment. A compound of formula (III) can also have a dual purpose in an application (e.g., a paint composition) as photostabilizing one or more photoactive compounds present in the application and to impart color to the application.

The compounds of formula (III), quite surprisingly, are able to impart color to a mixture of components. For example, the compound shown below in formula (IX)[1-ethylhexyl cyano(9H-fluoren-9-ylidene)acetate], is a brightly yellow colored compound.

(IX)

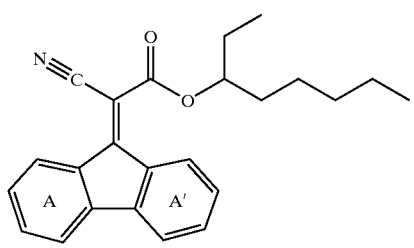

The color of such compounds can be controlled to reflect a particular wavelength of light, and thereby to appear to the visible eye a particular color, by placing at least one substituent on the one of the two aromatic rings of the fluorene core structure (labeled above as ring A and A'). For example, when two nitro ($NO_2$) groups are substituted at the 2 and 7 positions on the aromatic rings A and A' in the structure shown in formula (IX), the compound appears green in color.

The compounds of formula (III) can be used in various applications as a colorant to impart a particular color to a composition, including used as a colorant in coatings and inks. Preferably, when a compound of formula (III) is used as a colorant in inks, the compound is used as a colorant in a digital printing process. The use of compounds of formula (III) as a colorant provides the advantages that: (1) the compounds are extremely stable and will not degrade (lose its color) after they being applied on a substrate (e.g., paper); and (2) as described herein, the compounds of formula (III) are able to increase the photostability of the composition by absorbing the excited state energy of the other components in the composition and by absorbing UV-A light.

Thus, one embodiment of the inventions is a method of coloring an article, including adding to the article a compound of formula (III):

(III)

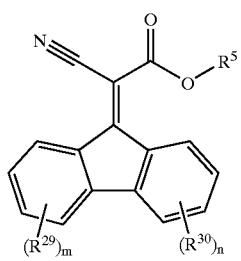

wherein $R^5$ is selected from the group consisting of $C_1$–$C_{30}$ alkyl, $C_3$–$C_8$ cycloalkyl, substituted alkyl, hydroxyalkyl, substituted hydroxyalkyl, ether, substituted ether, substituted cycloalkyl, aryl, heteroaryl, heterocycloalkyl, substituted aryl, substituted heteroaryl, substituted heterocycloalkyl, and amino; $R^{29}$ and $R^{30}$ are the same or different and are selected from the group consisting of hydrogen, $C_1$–$C_{30}$ alkyl, $C_3$–$C_8$ cycloalkyl, substituted alkyl, hydroxyalkyl, substituted hydroxyalkyl, ether, substituted ether, ester, aryl, heteroaryl, heterocycloalkyl, substituted aryl, substituted heteroaryl, substituted heterocycloalkyl, hydroxyl, alkoxy, halogen, cyano, imide, urethane, amide, and amino; and m and n are each in the range of 0 to 4. Preferably, $R^5$ is selected from the group consisting of $C_1$–$C_{20}$ branched chain alkyls, and $C_1$–$C_{30}$ hydroxyalkyls. More preferably, $R^5$ is selected from $C_2$–$C_8$ hydroxyalkyls, and in particular, $R^5$ is a selected from the group consisting of ethanol, propan-1-ol, propan-2-ol, 1-buatanol, methylpropan-1-ol, 2,2-dimethylpropan-1-ol, and 2-methylpropan-2-ol.

The compounds of formula (III) can be used as a colorant in a liquid, solid and/or a semi-solid (e.g., a gel) article. Furthermore, the compounds can be added to articles that include, for example, paints, inks (printing inks), films, and plastics. Preferably, the compounds of formula (III) are used as a colorant in an ink and, more preferably, as a colorant in a dry ink for use in a digital printer. When used in a film article, such as a wrapping, the compound of formula (III) acts as a colorant and also protects the material that it covers from UV radiation. When used as a colorant, the compound of formula (III) can be designed to be soluble in a component of the article by the design of substituents on the $R^5$ group. For example, the $R^5$ groups in the example shown above in formula (IX) (2-ethylhexyl) could optionally be substituted with one or more hydroxy groups to enhance the compound's solubility in an aqueous media. Thus, the compounds of formula (III) provide a great deal of flexibility with regards to the compatibility with various articles. To use a compound of formula (III) as a colorant, the compound can be added to the article or if the article is a mixture of components, the compound can be added to one of the components of the mixture prior to forming the final mixture. For example, in the process of forming plastics by thermosetting, a compound of formula (III) can be added to the plastic at various point in the thermosetting process and the compound will be incorporated in the structure of the plastic.

Another aspect of the invention is a compound selected from the group consisting of compounds of formula (IV) to (VI), and combinations thereof:

(IV)

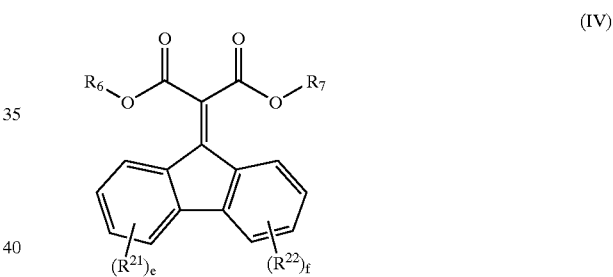

(V)

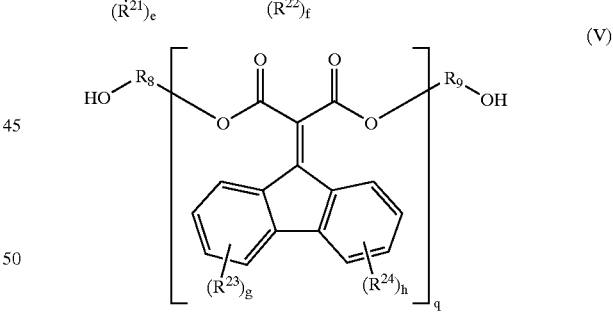

(VI)

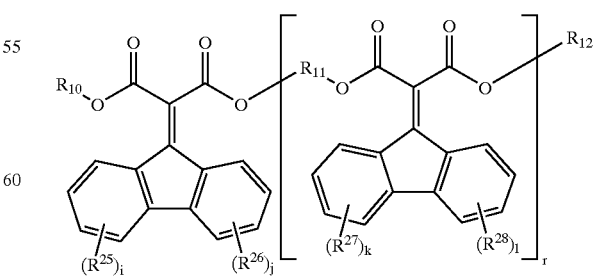

wherein, $R^6$ and $R^7$ are the same or different and are selected from the group consisting of $C_3$–$C_{30}$ alkyl, $C_3$–$C_8$ cycloalkyl, substituted alkyl, hydroxyalkyl, alkoxyalkyl, substituted cycloalkyl, ester, aryl, heteroaryl, heterocycloalkyl, substituted aryl, substituted heteroaryl, substituted heterocycloalkyl, cyano, and amino; $R^8$, $R^9$, $R^{10}$, $R^{11}$, and $R^{12}$ are the same or different and are selected from the group consisting of $C_1$–$C_{30}$ alkyl, $C_3$–$C_8$ cycloalkyl, substituted alkyl, hydroxyalkyl, alkoxyalkyl, substituted cycloalkyl, ester, aryl, heteroaryl, heterocycloalkyl, substituted aryl, substituted heteroaryl, substituted heterocycloalkyl, cyano, and amino; $C^{21}$, $C^{22}$, $C^{23}$, $C^{24}$, $C^{25}$, $C^{26}$, $C^{27}$, and $C^{28}$ are the same or different and are selected from the group consisting of hydrogen, $C_1$–$C_{30}$ alkyl, $C_3$–$C_8$ cycloalkyl, substituted alkyl, hydroxyalkyl, alkoxyalkyl, substituted cycloalkyl, ester, aryl, heteroaryl, heterocycloalkyl, substituted aryl, substituted heteroaryl, substituted heterocycloalkyl, hydroxyl, alkoxy, halogen, cyano, and amino; q and r are each in the range of 0 to 100; and e, f, g, h, i, j, and l are each in the range of 0 to 4.

Polyesters of formula (V) and formula (VI) can be prepared by the transesterification of a diester with a diol, for example as shown below for dimethyl isophthalate:

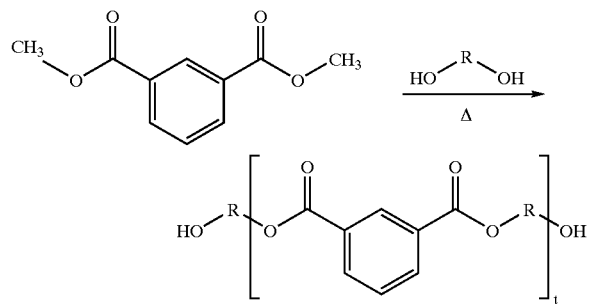

Transesterification can proceed to form a polymer under acidic, basic, or neutral conditions.

Compounds of formulae (IV) to (VI), quite surprisingly, are able to increase the stability of a photoactive compound in a sunscreen composition. Thus, preferably, one or more of a compound of formula (IV), a compound of formula (V), and a compound of formula (VI) is present in a sunscreen composition in a range of about 0.01% to about 30% by weight of the total weight of the composition, more preferably in a range of about 0.1% to about 10%.

Compounds of formula (III), quite surprisingly, are able to increase the photostability of a dibenzoylmethane derivative. Without intending to be limited to a particular mechanism, it is believed that a compound of formula (III) (e.g., octofluorene) stabilizes a dibenzoylmethane derivative by accepting the triplet energy of an excited state dibenzoylmethane derivative. This process of accepting the triplet excited energy of a dibenzoylmethane derivative converts the excited state dibenzoylmethane derivative to a ground state dibenzoylmethane derivative and allows the ground state dibenzoylmethane derivative to further absorb UV radiation. Thus, another embodiment of the invention is a method for photostabilizing a sunscreen composition including a dibenzoylmethane derivative, the method including the step of adding to the dibenzoylmethane derivative a photostabilizing amount of a compound of formula (III):

(III)

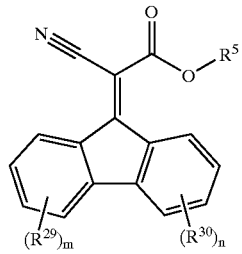

wherein $R^5$ is selected from the group consisting of $C_1$–$C_{30}$ alkyl, $C_3$–$C_8$ cycloalkyl, substituted alkyl, hydroxyalkyl, substituted hydroxyalkyl, ether, substituted ether, substituted cycloalkyl, aryl, heteroaryl, heterocycloalkyl, substituted aryl, substituted heteroaryl, substituted heterocycloalkyl, and amino; $R^{29}$ and $R^{30}$ are the same or different and are selected from the group consisting of hydrogen, $C_1$–$C_{30}$ alkyl, $C_3$–$C_8$ cycloalkyl, substituted alkyl, hydroxyalkyl, substituted hydroxyalkyl, ether, substituted ether, ester, aryl, heteroaryl, heterocycloalkyl, substituted aryl, substituted heteroaryl, substituted heterocycloalkyl, hydroxyl, alkoxy, halogen, cyano, imide, urethane, amide, and amino; and m and n are each in the range of 0 to 4. Preferably, $R^5$ is selected from $C_1$–$C_{30}$ hydroxyalkyls. More preferably, $R^5$ is selected from $C_2$–$C_8$ hydroxyalkyls, and in particular, $R^5$ is a selected from the group consisting of ethanol, propan-1-ol, propan-2-ol, 1-buatanol, methylpropan-1-ol, 2,2-dimethylpropan-1-ol, and 2-methylpropan-2-ol.

Likewise, compounds of formulae (IV) to (VI), quite surprisingly, are able to increase the photostability of a dibenzoylmethane derivative. Without intending to be limited to a particular mechanism, it is believed that a compound selected from the group consisting of compounds of formulae (IV) to (VI) is able to photostabilize a dibenzoylmethane derivative by accepting the triplet excited energy from an excited dibenzoylmethane derivative. Thus, another embodiment of the invention is a method for photostabilizing a dibenzoylmethane derivative, the method including the step of adding to the dibenzoylmethane derivative a photostabilizing amount of a compound selected from the group consisting of compounds of formulae (IV) to (VI), and combinations thereof:

(IV)

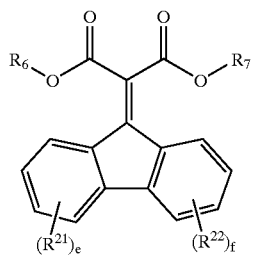

(V)

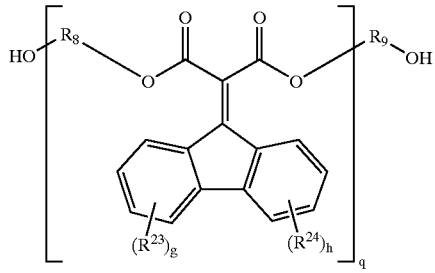

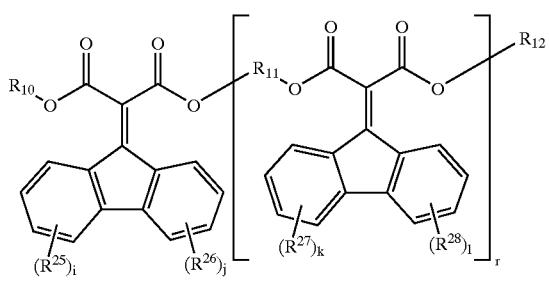

wherein, $R^6$, $R^7$, $R^8$, $R^9$, $R^{10}$, $R^{11}$, and $R^{12}$ are the same or different and are selected from the group consisting of $C_1$–$C_{30}$ alkyl, $C_3$–$C_8$ cycloalkyl, substituted alkyl, hydroxyalkyl, alkoxyalkyl, substituted cycloalkyl, ester, aryl, heteroaryl, heterocycloalkyl, substituted aryl, substituted heteroaryl, substituted heterocycloalkyl, cyano, and amino; $C^{21}$, $C^{22}$, $C^{23}$, $C^{24}$, $C^{25}$, $C^{26}$, $C^{27}$, and $C^{28}$ are the same or different and are selected from the group consisting of hydrogen, $C_1$–$C_{30}$ alkyl, $C_3$–$C_8$ cycloalkyl, substituted alkyl, hydroxyalkyl, alkoxyalkyl, substituted cycloalkyl, ester, aryl, heteroaryl, heterocycloalkyl, substituted aryl, substituted heteroaryl, substituted heterocycloalkyl, hydroxyl, alkoxy, halogen, cyano, and amino; q and r are each in the range of 0 to 100; and e, f, g, h, i, j, and l are each in the range of 0 to 4. Preferably, in a compound of formula (IV) $R^6$ and $R^7$ are the same and are selected from $C_3$–$C_{20}$ branch chain alkyls. More preferably, in a compound of formula (IV) $R^6$ and $R^7$ are the same and are 2-ethylhexane.

A compound selected from the group consisting of compounds of formulae (IV) to (VI), and combinations thereof, preferably is present in a sunscreen composition that includes a dibenzoylmethane derivative in a range of about 0.01% to about 30% by weight of the total weight of the composition, more preferably about 0.1% to about 10%, and still more preferably about 0.5% to about 5%. Compounds of formulae (IV) to (VI), quite surprisingly, are able also to act as a photoactive compound by absorbing UV radiation. Thus, is addition to photostabilizing a photoactive compound, compounds of formulae (IV) to (VI) can protect human skin from the harmful effects of UV radiation.

Compounds of formula (XI), quite surprisingly, are able also to act as a photoactive compound by absorbing UV radiation at a peak wavelength of absorbance at 325–350 nm. FIG. 1 shows the absorbance spectra for octofluorene (a compound of formula (XI), wherein $R^5$ is 2-ethylhexane). Accordingly, another embodiment of the invention is a method of protecting human skin from ultraviolet radiation comprising topically applying to the skin, in a cosmetically acceptable carrier, a compound of formula (XI):

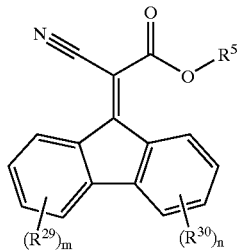

(XI)

wherein $R^5$ is selected from the group consisting of $C_1$–$C_{30}$ alkyl, $C_3$–$C_8$ cycloalkyl, substituted alkyl, hydroxyalkyl, substituted hydroxyalkyl, ether, substituted ether, substituted cycloalkyl, aryl, heteroaryl, heterocycloalkyl, substituted aryl, substituted heteroaryl, substituted heterocycloalkyl, and amino; $R^{29}$ and $R^{30}$ are the same or different and are selected from the group consisting of hydrogen, $C_1$–$C_{30}$ alkyl, $C_3$–$C_8$ cycloalkyl, substituted alkyl, hydroxyalkyl, substituted hydroxyalkyl, ether, substituted ether, ester, aryl, heteroaryl, heterocycloalkyl, substituted aryl, substituted heteroaryl, substituted heterocycloalkyl, hydroxyl, alkoxy, halogen, cyano, imide, urethane, amide, and amino; and m and n are each in the range of 0 to 4.

Polyesters, for example, can be prepared by the transesterification of a diester with a diol or by the esterification of a diacid with a diol, for example as shown below in formula (X) for dimethyl (diphenylmethylene)malonate:

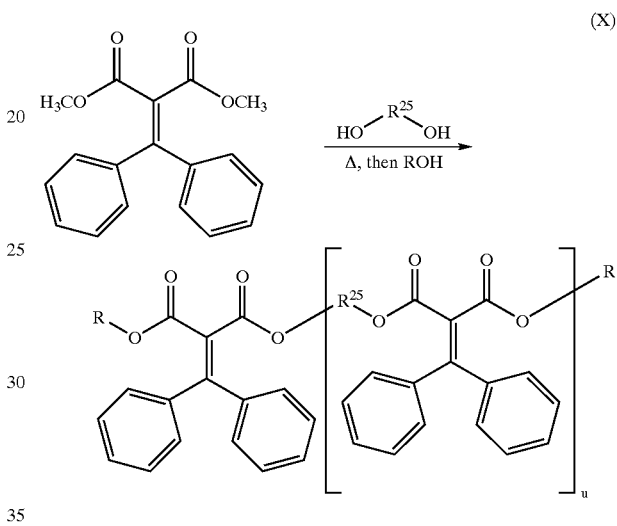

(X)

Transesterification can proceed to form a polymer under acidic, basic, or neutral conditions. When a polymer is prepared as shown above in formula (X), the polymerization can be terminated with the addition of a compound, such as a alcohol, that cannot react any further to elongate the polymer chain. It has been found, quite surprisingly, that a compound of formula (III) can be used to terminate a polymerization reaction. It has been found that one or more of a compound of formula (III) can be used to terminate polymerizations of polyesters, polyamides, polyolefins, and polyurethanes, for example. Thus, another aspect of the invention is a method of making a polymer, including terminating a polymer chain with a compound selected from the group consisting of compounds of formula (III):

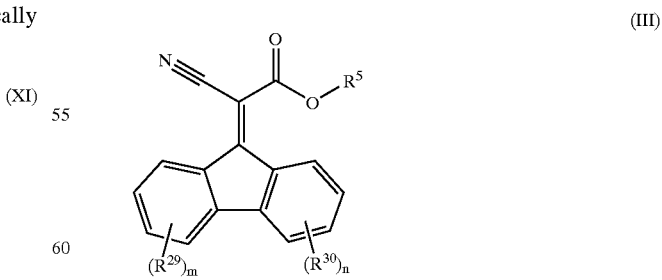

(III)

wherein $R^5$ is selected from the group consisting of $C_1$–$C_{30}$ alkyl, $C_3$–$C_8$ cycloalkyl, substituted alkyl, hydroxyalkyl, substituted hydroxyalkyl, ether, substituted ether, substituted cycloalkyl, aryl, heteroaryl, heterocycloalkyl, substituted aryl, substituted heteroaryl, substituted heterocycloalkyl, and amino; $R^{29}$ and $R^{30}$ are the same or different and are selected from the group consisting of hydrogen, $C_1$–$C_{30}$ alkyl, $C_3$–$C_8$ cycloalkyl, substituted alkyl, hydroxyalkyl, substituted hydroxyalkyl, ether, substituted ether, ester, aryl, heteroaryl, heterocycloalkyl, substituted aryl, substituted heteroaryl, substituted heterocycloalkyl, hydroxyl, alkoxy, halogen, cyano, imide, urethane, amide, and amino; and m and n are each in the range of 0 to 4. Preferably, the polymer chain is selected from the group consisting of polyesters, polyamides, polyolefins, polyurethanes, and combinations thereof. For example, a compound of formula (III) can be incorporated into a synthetic plastic, such as polystyrene, as a terminator in the plasticization process; and by terminating the polymer, the compound becomes part of the plastic and also terminates the plasticization process. It has been found that polymers formed according to this method can be used to photostabilize a photoactive compound in a sunscreen composition.

EXAMPLES

The following examples are provided to illustrate the invention but are not intended to limit the scope of the invention.

Example 1

Octofluorene was prepared by placing 9-fluorenone (130.0 g, 0.721 mole, 1.0 mole equivalence), 2-ethylhexyl cyanoacetate (143.7 g, 0.728 mole, 1.01 eq), ammonium acetate (5.0 g, 0.065 mole, 0.09 eq), toluene (450 ml), and acetic acid (90 ml) into a 1 liter 3-neck round bottom flask (the reaction flask). The reaction flask was assembled with mechanical stirrer, condenser, Dean-Stark receiver, thermometer, and nitrogen inlet. The reaction mixture was then heated to reflux and water was removed continuously. The water phase (29 ml; expected water from reaction was 13 ml) was removed and the reaction was refluxed for 18 h. When gas chromatography (GC) showed complete consumption of one of the reagents, the reaction mixture was cooled to room temperature, washed with water (2×400 ml), diluted sodium bicarbonate (400 ml), and water (300 ml). All water washings were discarded and the organic phase was placed back in the reaction flask and all solvents were removed by distillation under vacuum. Traces of toluene were removed by steam distillation. The desired product, octofluorene, (270 g, 96% pure as determined by GC) was dried, and filtered over CELITE filter medium.

Example 2

A series of sunscreen compositions was prepared by mixing the ingredients and concentrations (formulations) shown in Table II below:

TABLE II

| Ingredients | 4% Octocrylene | 4% Octofluorene |
|---|---|---|
| Oil Phase | | |
| Avobenzone | 2.00% | 2.00% |
| Octyl salicylate | 5.00% | 5.00% |
| Octyl-p-methoxy Cinnamate | 7.50% | 7.50% |
| Octofluorene | | 3.60% |
| Octocrylene | 3.60% | |
| $C_{12}$–$C_{15}$ alkyl benzoates | 10.00% | 10.00% |
| Bodying Agent And Film-Former | | |
| Stearyl alcohol | 1.00% | 1.00% |
| $C_{30}$–$C_{38}$ olefin/Isopropyl maleate/MA copolymer | 2.00% | 2.00% |

TABLE II-continued

| Ingredients | 4% Octocrylene | 4% Octofluorene |
|---|---|---|
| Emulsifiers | | |
| Steareth 21 | 0.32% | 0.25% |
| Steareth 2 | 0.30% | 0.25% |
| Polyglyceryl-3 methyl glucose distearate | 3.00% | 3.00% |
| Water Phase | | |
| Disodium EDTA | 0.05% | 0.05% |
| Glycerin | 3.00% | 3.00% |
| Methylpropanediol | 2.00% | 2.00% |
| Phenoxyethanol & parabens | 0.60% | 0.60% |
| Stabilizer and Neutralizer | | |
| Carbomer | 0.20% | 0.20% |
| Sodium hydroxide (25% solution) | 0.32% | 0.32% |
| Water | 59.11% | 59.23% |

Oil-in-water emulsions were created, wherein the aqueous phase was made up of water, the water phase ingredients, the stabilizer and neutralizer, the emulsifiers, and the bodying agent and film-former listed above. The resulting sunscreens were tested for photostability by measuring absorbance on a Labsphere UV-1000S Ultraviolet Transmittance Analyzer (software version 1.27) before and after irradiation with a Solar Light Company model 16S solar simulator (equipped with a WG 320 filter to transmit radiation greater than 290 nm) in 5 MED increments up to 30 MED. Output was monitored by a PMA 2105 UV-B DCS Detector (biologically weighted) and controlled by a PMA 2100 Automatic Dose Controller (Solar Light Co.).

To test stability, a slide was positioned on the UV transmittance analyzer using registration marks, and a scan of a 1 cm spot on the slide was performed. The slide was then transferred to a holder placed adjacent to the solar simulator and, using a calipers, was positioned such that the beam of UV radiation exiting the solar simulator illuminated the same 1 cm spot on the slide. The following software settings were used: UV-B=290–320 nm; UV-A=320–400 nm. Following an exposure of 5 MED, the slide was again placed in position on the UV transmittance analyzer, and a scan of the exposed spot was performed. The procedure was repeated on the same 1 cm spot on the slide until the desired total radiation dosage was achieved.

Figure 3:
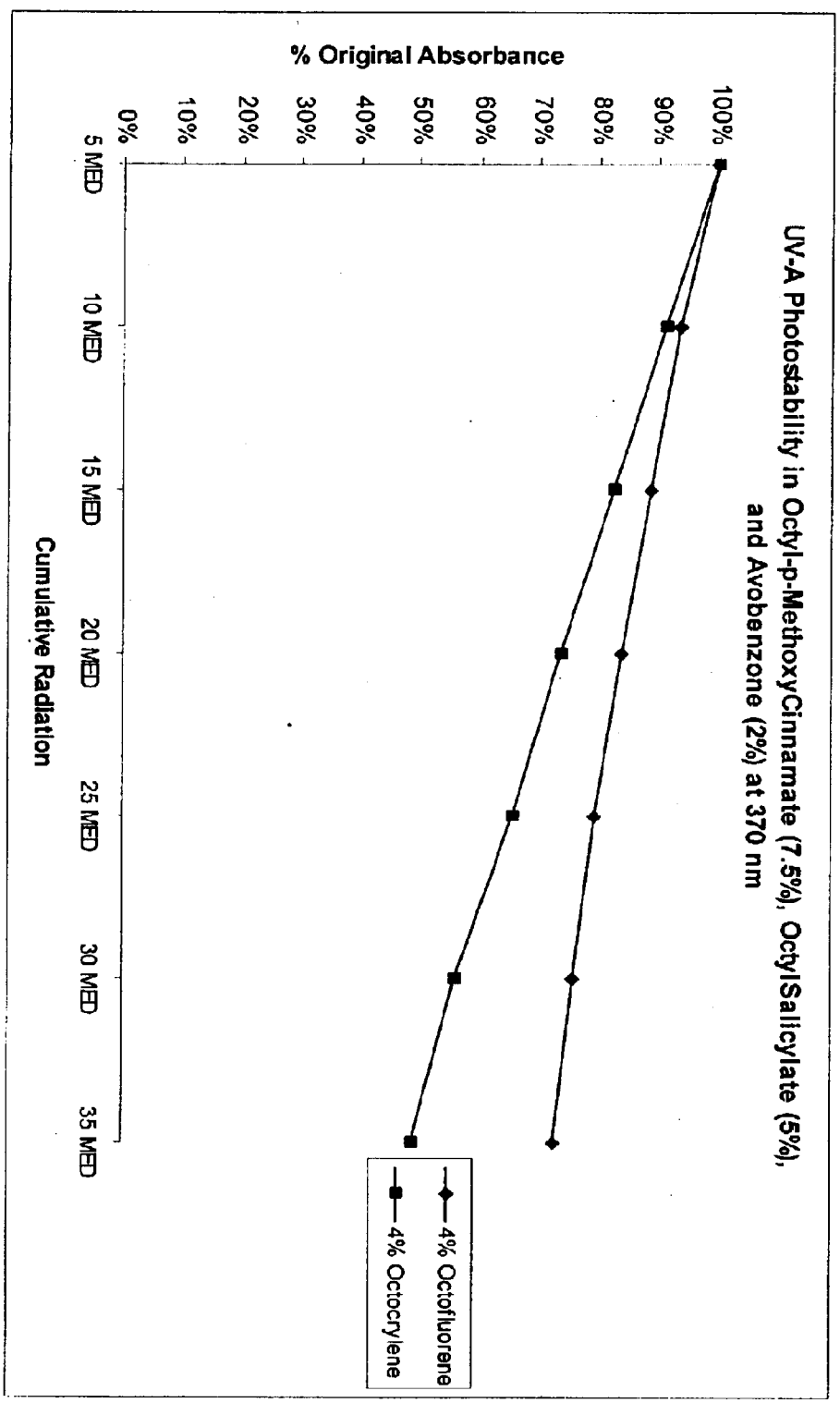
FIG. 3 is a graph of the percent of the original absorbance of sunscreen compositions including various amounts of octocrylene and octofluorene. The octocrylene and octofluorene were prepared in sunscreen compositions including 7.5% by weight of octyl-p-methoxycinnamate, 5% by weight of octyl salicylate and 2% by weight of avobenzone, wherein the percent absorbance is measured at a wavelength of 370 nm and at various intervals of exposure to radiation up to and including 35 MED.

FIG. 3 is a graph of the percent absorbance of the sunscreen compositions listed in Table II at various intervals of exposure to radiation. As shown in FIG. 3, a composition including 4% octofluorene is more photostable than a composition including 4% octocrylene (after 35 MED exposure to UV radiation at a wavelength of 370 nm).

Example 4

A series of sunscreen compositions were prepared by mixing the ingredients and concentrations (formulations) shown in Table III below:

TABLE III

| Ingredients | 4% OF | 4% OC | 2% OF | 1% OF | Control |
|---|---|---|---|---|---|
| Oil Phase | | | | | |
| Avobenzone | 2.00% | 2.00% | 2.00% | 2.00% | 2.00% |
| Octyl methoxycinnamate | 4.00% | 4.00% | 4.00% | 4.00% | 4.00% |
| Octofluorene | 4.00% | | 2.00% | 1.00% | |

TABLE III-continued

| Ingredients | 4% OF | 4% OC | 2% OF | 1% OF | Control |
|---|---|---|---|---|---|
| Octocrylene | | 4.00% | | | |
| $C_{12}$–$C_{15}$ alkyl benzoates | 10.00% | 10.00% | 12.00% | 13.00% | 14.00% |
| Avobenzone | 2.00% | 2.00% | 2.00% | 2.00% | 2.00% |
| Octyl methoxycinnamate | 4.00% | 4.00% | 4.00% | 4.00% | 4.00% |
| Bodying Agent And Film-Former | | | | | |
| Stearyl alcohol | 1.00% | 1.00% | 1.00% | 1.00% | 1.00% |
| $C_{30}$–$C_{38}$ olefin/Isopropyl maleate/MA copolymer | 2.00% | 2.00% | 2.00% | 2.00% | 2.00% |
| Emulsifiers | | | | | |
| Steareth 21 | 0.30% | 0.31% | 0.31% | 0.32% | 0.32% |
| Steareth 2 | 0.20% | 0.19% | 0.19% | 0.18% | 0.18% |
| Polyglyceryl-3 methyl glucose distearate | 3.00% | 3.00% | 3.00% | 3.00% | 3.00% |
| Water Phase | | | | | |
| Disodium EDTA | 0.05% | 0.05% | 0.05% | 0.05% | 0.05% |
| Glycerin | 3.00% | 3.00% | 3.00% | 3.00% | 3.00% |
| Methylpropanediol | 2.00% | 2.00% | 2.00% | 2.00% | 2.00% |
| Phenoxyethanol & parabens | 0.60% | 0.60% | 0.60% | 0.60% | 0.60% |
| Stabilizer and Neutralizer | | | | | |
| Carbomer | 0.20% | 0.20% | 0.20% | 0.20% | 0.20% |
| Sodium hydroxide (25% solution) | 0.28% | 0.28% | 0.28% | 0.28% | 0.28% |
| Water | 67.37% | 67.37% | 67.37% | 67.37% | 67.37% |

Oil-in-water emulsions were created and the stabilities of the compositions of this example were tested according to the procedures described above in Example 2.

Figure 4:
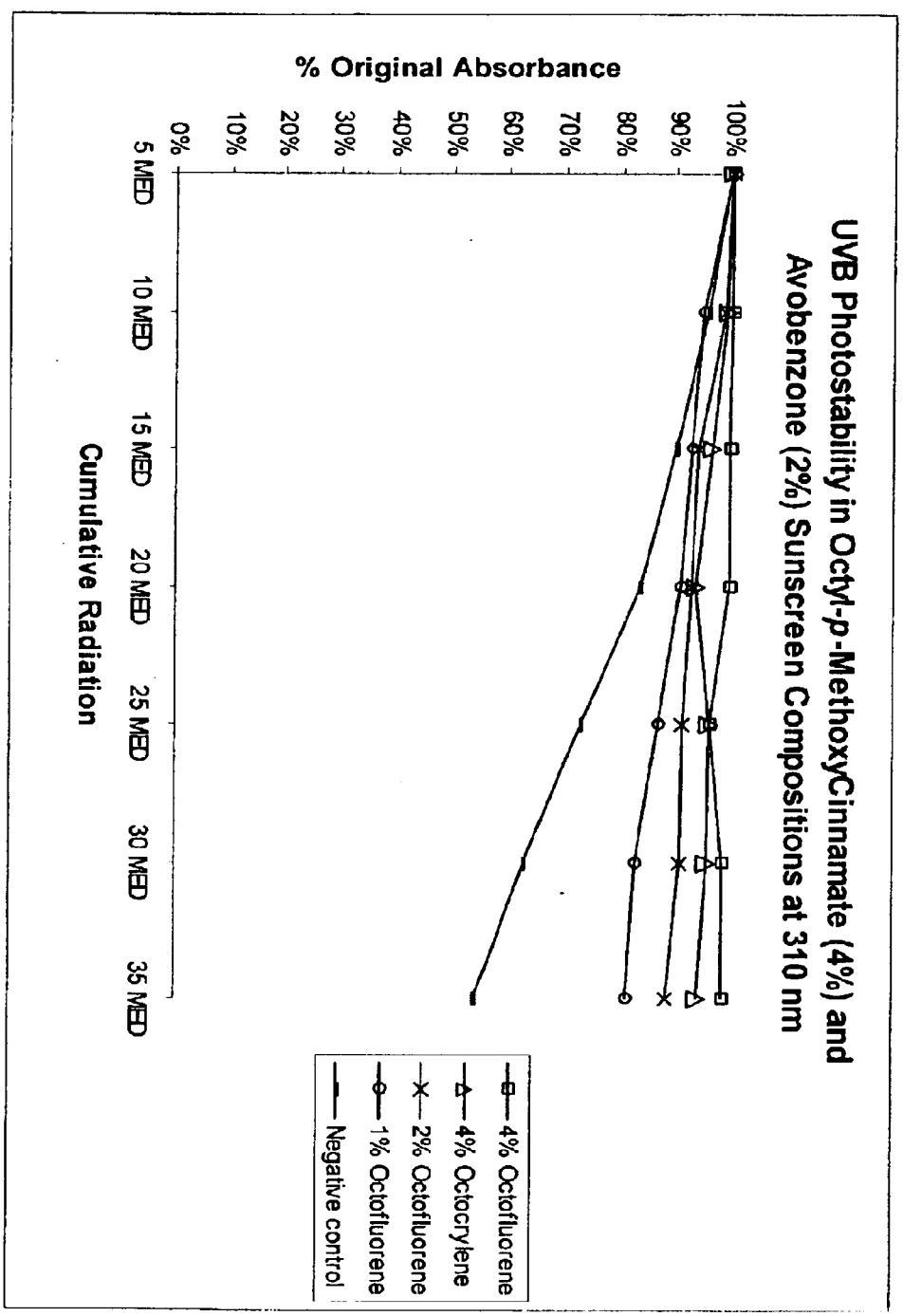
FIG. 4 is a graph of the percent of the original absorbance of sunscreen compositions including octocrylene and octofluorene at various concentrations in sunscreen compositions including 4% by weight of octyl-p-methoxycinnamate and 2% by weight of avobenzone, wherein the percent absorbance is measured at a wavelength of 310 nm and at various intervals of exposure to radiation, up to and including 35 MED.

FIG. 4 is a graph of the percent absorbance of the sunscreen compositions listed in Table III at various intervals of exposure to radiation. FIG. 4 shows the photostability of sunscreen compositions including various levels octocrylene and/or octofluorene. In particular, the absorbance of the sunscreen compositions at a wavelength of 310 nm was measured, which is the approximate peak absorbance for octyl-p-methoxy cinnamate; thus, photostability data shown in FIG. 4 primarily represent the photostability of the UV-B photoactive compound, octyl-p-methoxy cinnamate. As discussed above, when a dibenzoylmethane derivative is combined in a sunscreen composition including octyl-p-methoxy cinnamate, the dibenzoylmethane derivative becomes particularly unstable. However, as shown in FIG. 4, a stable sunscreen composition was formed in a composition including 4% octofluorene.

Example 5

A series of sunscreen compositions were prepared by mixing the ingredients and concentrations (formulations) shown in Table IV below:

TABLE IV

| Ingredients | 4% OF | 4% OC | 2% OF | 1% OF | Neg. Control |
|---|---|---|---|---|---|
| Oil Phase | | | | | |
| Avobenzone | 2.00% | 2.00% | 2.00% | 2.00% | 2.00% |
| Octyl-p-methoxy Cinnamate | 4.00% | 4.00% | 4.00% | 4.00% | 4.00% |
| Octofluorene | 4.00% | | 2.00% | 1.00% | |

TABLE IV-continued

| Ingredients | 4% OF | 4% OC | 2% OF | 1% OF | Neg. Control |
|---|---|---|---|---|---|
| Octocrylene | | 4.00% | | | |
| $C_{12}$–$C_{15}$ alkyl benzoates | 10.00% | 10.00% | 12.00% | 13.00% | 14.00% |
| Bodying Agent And Film-Former | | | | | |
| Stearyl alcohol | 1.00% | 1.00% | 1.00% | 1.00% | 1.00% |
| C30–38 olefin/Isopropyl maleate/MA copolymer | 2.00% | 2.00% | 2.00% | 2.00% | 2.00% |
| Emulsifiers | | | | | |
| Steareth 21 | 0.32% | 0.32% | 0.70% | 0.70% | 0.70% |
| Steareth 2 | 0.18% | 0.18% | 0.40% | 0.40% | 0.40% |
| Polyglyceryl-3 methyl glucose distearate | 3.00% | 3.00% | 3.00% | 3.00% | 3.00% |
| Water Phase | | | | | |
| Disodium EDTA | 0.05% | 0.05% | 0.05% | 0.05% | 0.05% |
| Glycerin | 3.00% | 3.00% | 3.00% | 3.00% | 3.00% |
| Methylpropanediol | 2.00% | 2.00% | 2.00% | 2.00% | 2.00% |
| Phenoxyethanol & parabens | 0.60% | 0.60% | 0.60% | 0.60% | 0.60% |
| Stabilizer and Neutralizer | | | | | |
| Carbomer | 0.20% | 0.20% | 0.20% | 0.20% | 0.20% |
| Sodium hydroxide (25% solution) | 0.28% | 0.28% | 0.28% | 0.28% | 0.28% |
| Water | 66.37% | 66.37% | 59.77% | 59.77% | 64.77% |

Figure 5:
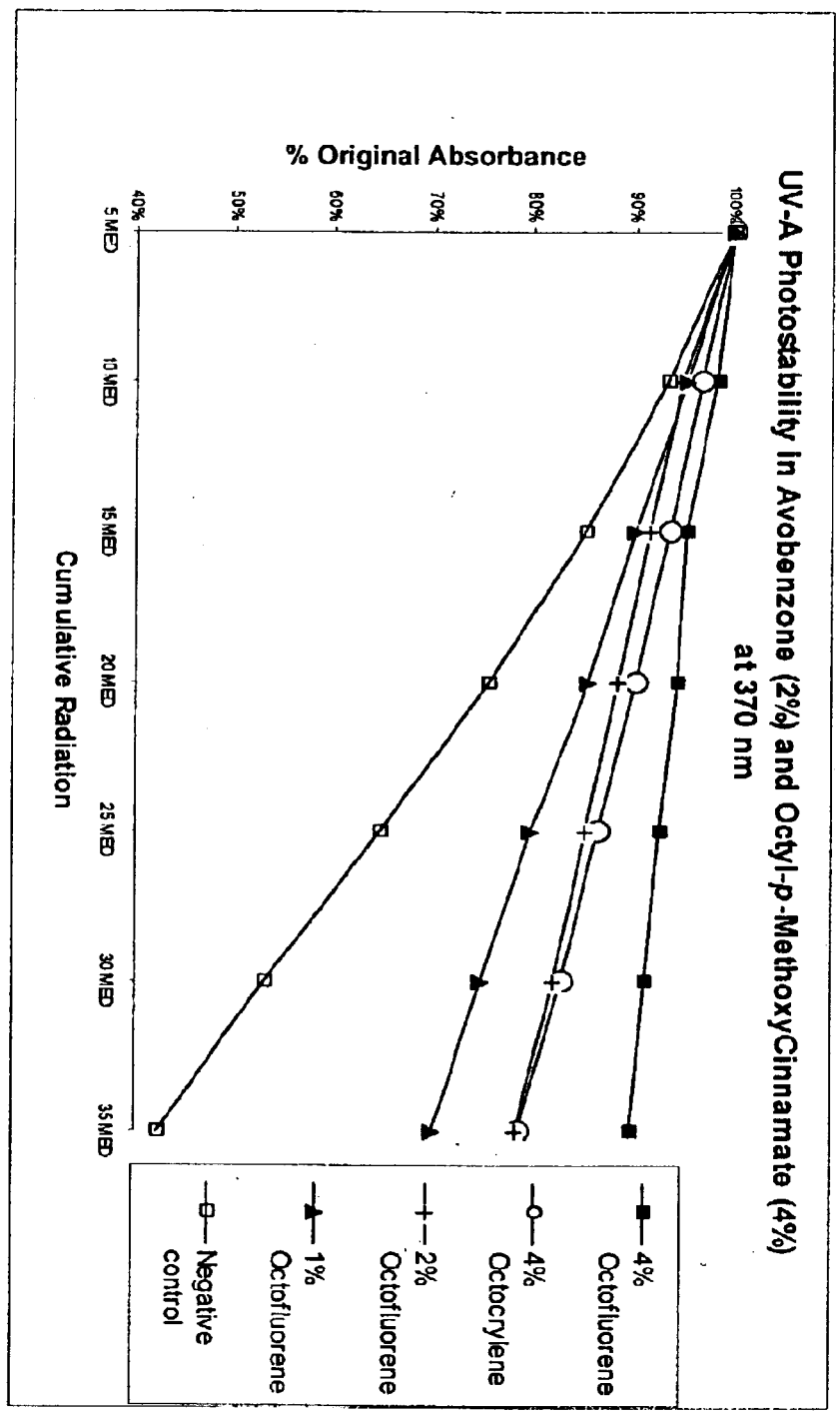
FIG. 5 is a graph of the percent of the original absorbance of compositions including octocrylene and octofluorene at various concentrations in sunscreen compositions including 4% by weight of octyl-p-methoxycinnamate and 2% by weight of avobenzone, wherein the percent absorbance is measured at a wavelength of 370 nm and at various intervals of exposure to radiation, up to and including 35 MED units.

Oil-in-water emulsions were created and the stabilities of the compositions of this example were tested according to the procedures described above in Example 2. FIG. 5 is a graph of the percent absorbance of the sunscreen compositions listed in Table IV at various intervals of exposure to radiation.

Example 6

A series of sunscreen compositions were prepared by mixing the ingredients and concentrations (formulations) shown in Table V below:

TABLE V

| Ingredients | 5% DEHN, 0.45% OF | 4% OC | 5% DEHN | Control |
|---|---|---|---|---|
| Oil Phase | | | | |
| Avobenzone | 2.00% | 2.00% | 2.00% | 2.00% |
| Octyl salicylate | 5.00% | 5.00% | 5.00% | 5.00% |
| Diethylhexyl 2,6-naphthalate | 5.00% | | 5.00% | |
| Octofluorene | 0.45% | | | |
| Octocrylene | | 4.00% | | |
| $C_{12}$–$C_{15}$ alkyl benzoates | | 10.00% | 10.00% | 10.00% |
| Octyldodecyl neopentanoate | | | 5.00% | |
| Polyisobutene | | | | 5.00% |
| Diethylhexyl malate | 9.55% | | | |
| Bodying Agent And Film-Former | | | | |
| Stearyl alcohol | 1.00% | 1.00% | 1.00% | 1.00% |
| $C_{30}$–$C_{38}$ olefin/ Isopropyl maleate/MA copolymer | 2.00% | 2.00% | 2.00% | 2.00% |
| Emulsifiers | | | | |
| Steareth 21 | 0.32% | 0.32% | 0.70% | 0.70% |
| Steareth 2 | 0.18% | 0.18% | 0.40% | 0.40% |
| Polyglyceryl-3 methyl glucose distearate | 3.00% | 3.00% | 3.00% | 3.00% |

TABLE V-continued

| Ingredients | 5% DEHN, 0.45% OF | 4% OC | 5% DEHN | Control |
|---|---|---|---|---|
| Water Phase | | | | |
| Disodium EDTA | 0.05% | 0.05% | 0.05% | 0.05% |
| Glycerin | 3.00% | 3.00% | 3.00% | 3.00% |
| Methylpropanediol | 2.00% | 2.00% | 2.00% | 2.00% |
| Phenoxyethanol & parabens | 0.60% | 0.60% | 0.60% | 0.60% |
| Stabilizer and Neutralizer | | | | |
| Carbomer | 0.20% | 0.20% | 0.20% | 0.20% |
| Sodium hydroxide (25% solution) | 0.28% | 0.28% | 0.28% | 0.28% |
| Water | 65.37% | 66.37% | 59.77% | 64.77% |

Oil-in-water emulsions were created and the stabilities of the compositions of this example were tested according to the procedures described above in Example 2.

Figure 6:
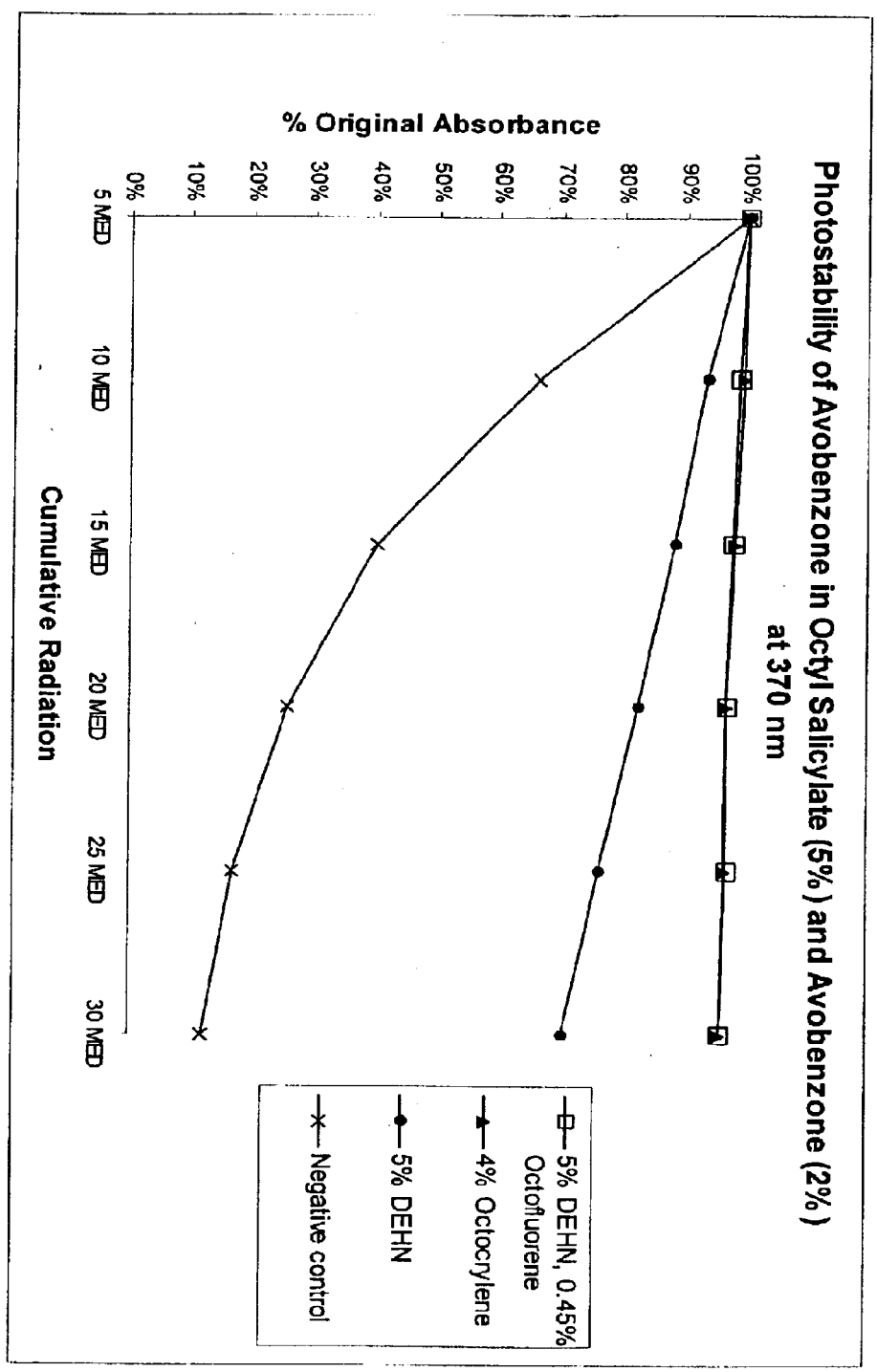
FIG. 6 is a graph of the percent of the original absorbance of the sunscreen compositions listed in Table II, wherein the percent absorbance is measured at a wavelength of 370 nm and at various intervals of exposure to radiation, up to and including 30 MED.

FIG. 6 is a graph of the percent absorbance of the sunscreen compositions listed in Table V at various intervals of exposure to radiation. This figure shows the increase in stability of absorbance at 370 nm by the addition of very low levels of octofluorene to a composition including avobenzone and 5% by weight of diethylhexyl naphthalate (DEHN).

Without intending to be limited to a particular mechanism of action, it is believed that in a composition including a diester or polyester of naphthalene dicarboxylic acid compound such as DEHN and a derivative of fluorene, depending on the concentrations of the derivative of fluorene, one of the compounds would exclusively dominate the photostability profile. Thus, one would expect that at high concentration of a diester or polyester of naphthalene dicarboxylic acid compound, the addition of low and very low levels of one or more derivatives of fluorene would not increase the overall photostability of the dibenzoylmethane derivative.

It has been found, quite surprisingly however, that at low (e.g., 1% by weight) and very low levels (e.g., less that 0.5% by weight) of a derivative of fluorene, the combination can work synergistically to provide even greater stabilization of a dibenzoylmethane derivative than would be expected. Without intending to be limited to any particular mechanism of operation, it is believed that the relatively high concentration of diester or polyester of naphthalene dicarboxylic acid provides a sufficient amount of the diesters or polyesters in proximity to dibenzoylmethane derivatives and, as the dibenzoylmethane derivatives are excited to their triplet excited states, the diester or polyester accepts the triplet excited energy at a sufficient rate to substantially reduce or prevent degradation of the dibenzoylmethane derivative.

At the same time, however, the relatively low amount of a derivative of fluorene is believed to rapidly accept triplet excited energy from the relatively numerous diester or polyester molecules around it in solution, and very rapidly dissipate the energy through a rapid isomerization mechanism, thus generating ground state diesters or polyesters of naphthalene dicarboxylic acid that are once again able to accept excited state energy from an excited dibenzoylmethane derivative. Thus, the weight ratio of dibenzoylmethane derivative to a derivative of fluorene is, preferably, at least about 6:1, for example at least 10:1.

In addition, as shown in FIG. 6, a stable composition was formed in a composition including low levels of octofluorene and 5% by weight of DEHN.

Example 7

A series of sunscreen compositions were prepared by mixing the ingredients and concentrations (formulations) shown in Table VI below:

TABLE VI

| Ingredients | 5% DEHN, 0.45% OF | 4% OC | 5% DEHN, 0.45% OC | 5% DEHN Alone | D.C. Adjustment Alone | Control |
|---|---|---|---|---|---|---|
| Oil Phase | | | | | | |
| Avobenzone | 2.00% | 2.00% | 2.00% | 2.00% | 2.00% | 2.00% |
| Octyl salicylate | 5.00% | 5.00% | 5.00% | 5.00% | 5.00% | 5.00% |
| Diethylhexyl 2,6-naphthalate | 5.00% | | 5.00% | 5.00% | | |
| Octofluorene | 0.45% | | | | | |
| Octocrylene | | 4.00% | 0.45% | | | |
| $C_{12}$–$C_{15}$ alkyl benzoates | | 10.00% | | 10.00% | | 10.00% |
| Octyldodecyl neopentanoate | | | | 5.00% | | |
| Polyisobutene | | | | | | 5.00% |
| Diethylhexyl malate | 9.55% | | 9.55% | | 10.00% | |
| Butyloctyl dimer with HDI | | | | | 5.00% | |
| Bodying Agent And Film-Former | | | | | | |
| Stearyl alcohol | 1.00% | 1.00% | 1.50% | 1.00% | 1.20% | 1.00% |
| $C_{30}$–$C_{38}$ olefin/Isopropyl maleate/MA copolymer | 2.00% | 2.00% | 2.00% | 2.00% | 2.00% | 2.00% |
| Emulsifiers | | | | | | |
| Steareth 21 | 0.32% | 0.32% | 0.33% | 0.70% | 0.55% | 0.70% |
| Steareth 2 | 0.18% | 0.18% | 0.18% | 0.40% | 0.7% | 0.40% |
| Polyglyceryl-3 methyl glucose distearate | 3.00% | 3.00% | 3.00% | 3.00% | 3.00% | 3.00% |

TABLE VI-continued

| Ingredients | 5% DEHN, 0.45% OF | 4% OC | 5% DEHN, 0.45% OC | 5% DEHN Alone | D.C. Adjustment Alone | Control |
|---|---|---|---|---|---|---|
| Water Phase | | | | | | |
| Disodium EDTA | 0.05% | 0.05% | 0.50% | 0.05% | 5.00% | 0.05% |
| Glycerin | 3.00% | 3.00% | 3.00% | 3.00% | 3.00% | 3.00% |
| Methylpropanediol | 2.00% | 2.00% | 2.00% | 2.00% | 2.00% | 2.00% |
| Phenoxyethanol & parabens | 0.60% | 0.60% | 0.60% | 0.60% | 0.60% | 0.60% |
| Stabilizer and Neutralizer | | | | | | |
| Carbomer | 0.20% | 0.20% | 0.20% | 0.20% | 0.20% | 0.20% |
| Sodium hydroxide (25% solution) | 0.28% | 0.28% | 0.29% | 0.28% | 0.28% | 0.28% |
| Water | 65.37% | 66.37% | 64.40% | 59.77% | 59.47% | 64.77% |

Oil-in-water emulsions were created and the stabilities of the compositions of this example were tested according to the procedures described above in Example 2.

Figure 7:
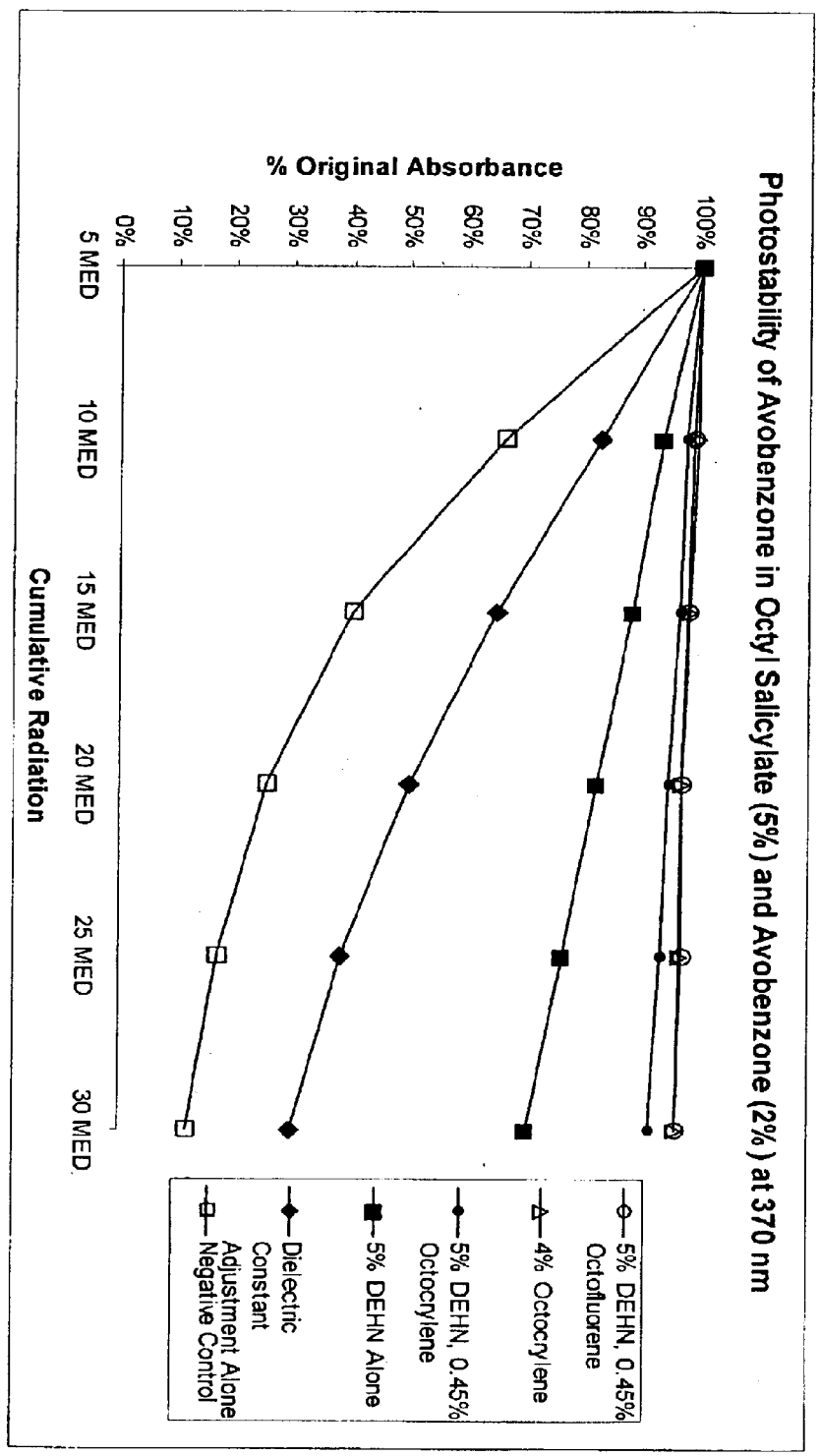
FIG. 7 is a graph of the percent of the original absorbance of compositions including octofluorene, octocrylene, diethylhexyl-2,6-naphthalate (DEHN) in a composition including 5% by weight of octyl salicylate and 2% by weight of avobenzone wherein highly polar solvent were included in the oil-phase of the composition to raise the dielectric constant of the oil-phase, and the percent absorbance is measured at a wavelength of 370 nm and at various intervals of exposure to radiation, up to and including 30 MED.

FIG. 7 is a graph of the percent absorbance of the sunscreen compositions including various combinations of octocrylene, octofluorene, and DEHN as listed in Table VI and at various intervals of exposure to radiation. As described in Example 6, it has been found, quite surprisingly, that at low (e.g., 1% by weight) and very low levels (e.g., less that 0.5% by weight) of a derivative of fluorene, the combination works synergistically to provide even greater stabilization of a dibenzoylmethane derivative than would be expected. As shown in FIG. 7, a stable sunscreen composition was formed by the combination of 5% DEHN and 0.45% of octofluorene into a sunscreen composition.

Example 8

A series of sunscreen compositions were prepared by mixing the ingredients and concentrations (formulations) shown in Table VII below:

TABLE VII

| Ingredients | 1% DPFM | 2% DPFM | 3% DPFM | Control |
|---|---|---|---|---|
| Oil phase | | | | |
| Avobenzone | 2.00% | 2.00% | 2.00% | 2.00% |
| Octyl salicylate | 5.00% | 5.00% | 5.00% | 5.00% |
| Diisopropyl fluorenmalonate | 1.00% | 2.00% | 3.00% | |
| $C_{12}$–$C_{15}$ alkyl benzoates | 14.00% | 13.00% | 12.00% | 10.00% |
| Polyisobutene | | | | 5.00% |
| Dimethyl capramide | | | 1.00% | |
| Bodying Agent And Film-Former | | | | |
| Stearyl alcohol | 1.00% | 1.00% | 1.00% | 1.00% |
| $C_{30}$–$C_{38}$ olefin/Isopropyl maleate/MA copolymer | 2.00% | 2.00% | 2.00% | 2.00% |
| Emulsifiers | | | | |
| Steareth 21 | 0.38% | 0.28% | 0.28% | 0.70% |
| Steareth 2 | 0.18% | 0.22% | 0.22% | 0.40% |
| Polyglyceryl-3 methyl glucose distearate | 3.00% | 3.00% | 3.00% | 3.00% |
| Water Phase | | | | |
| Disodium EDTA | 0.05% | 0.05% | 0.05% | 0.05% |
| Glycerin | 3.00% | 3.00% | 3.00% | 3.00% |
| Methylpropanediol | 2.00% | 2.00% | 2.00% | 2.00% |
| Phenoxyethanol & parabens | 0.60% | 0.60% | 0.60% | 0.60% |

TABLE VII-continued

| Ingredients | 1% DPFM | 2% DPFM | 3% DPFM | Control |
|---|---|---|---|---|
| Stabilizer and Neutralizer | | | | |
| Carbomer | 0.20% | 0.20% | 0.20% | 0.20% |
| Sodium hydroxide (25% solution) | 0.28% | 0.28% | 0.28% | 0.28% |
| Water | 65.31% | 65.37% | 64.37% | 64.77% |

Oil-in-water emulsions were created and the stabilities of the compositions of this example were tested according to the procedures described above in Example 2.

Figure 8:
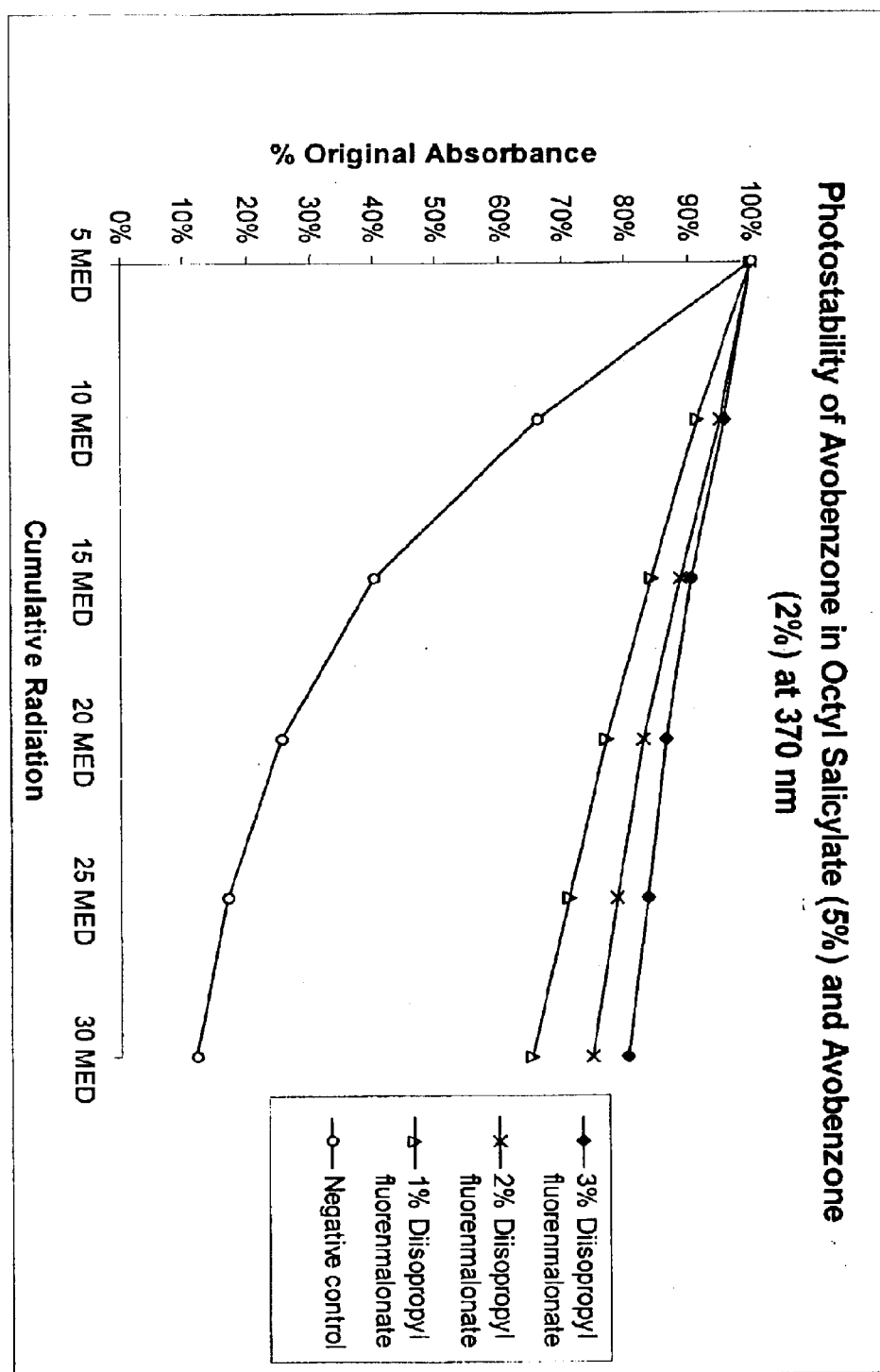
FIG. 8 is a graph of the percent of the original absorbance of the sunscreen compositions listed in Table VII, wherein the percent absorbance is measured at a wavelength of 370 nm and at various intervals of exposure to radiation, up to and including 30 MED.

FIG. 8 is a graph of the percent absorbance of the sunscreen compositions listed in Table VII at various intervals of exposure to radiation. FIG. 8 shows the photostability of sunscreen compositions including various levels of diiusopropyl fluorenmalonate (diisopropyl 9H-fluoren-9-ylidenemalonate, a compound of formula IV wherein $R^6$, $R^7$ are the same and are isopropane). As shown in FIG. 8, as the amount of diisopropyl fluorenmalonate is increased, the photostability of the photoactive compounds in the composition (e.g., avobenzone) increases.

The foregoing description is given for clearness of understanding only, and no unnecessary limitations should be understood therefrom, as modifications within the scope of the invention may be apparent to those having ordinary skill in the art.

What is claimed is:
1. A compound of formula (III),

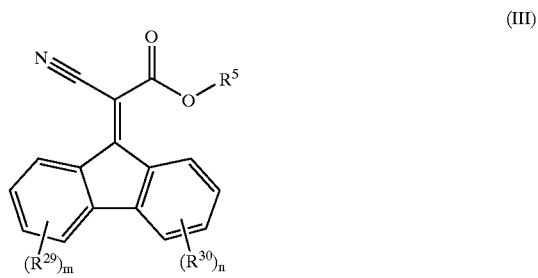

wherein $R^5$ is selected from the group consisting of $C_3$–$C_{30}$ alkyl, $C_3$–$C_8$ cycloalkyl, substituted alkyl, hydroxyalkyl, substituted hydroxyalkyl, ether, substituted ether, substituted cyoloalkyl, aryl, substituted aryl, and amino; $R^{29}$ and $R^{30}$ are the same or different and are selected from the group consisting of hydrogen, $C_1$–$C_{30}$ alkyl, $C_3$–$C_8$ cycloalkyl, substituted alkyl, hydroxyalkyl, substituted hydroxyalkyl, ether, substituted ether, hydroxyl, alkoxy, halogen, cyano, imide, urethane, amide, and amino; and m and n are each in the range of 0 to 4.

2. The compound of claim 1, wherein $R^5$ is selected from $C_3$–$C_{20}$ branched chain alkyls.

3. The compound of claim 1, wherein $R^5$ is selected from $C_1$–$C_{30}$ hydroxyalkyls.

4. The compound of claim 3, wherein $R^5$ is selected from $C_2$–$C_8$ hydroxyalkyls.

5. The compound of claim 4, wherein the alkyl of said $C_2$–$C_8$ hydroxyalkyls is selected from the group consisting of $CH_2CH_2$, $CH_2CH_2CH_2$, $CH_2CH_2CH_2CH_2$, $CH_2CH(CH_3)CH_2$, and $CH_2C(CH_3)_2CH_2$.

6. A method of protecting a surface from ultraviolet radiation compxising topically applying to said surface; in a cosmetically acceptable carrier, a compound of formula (XI):

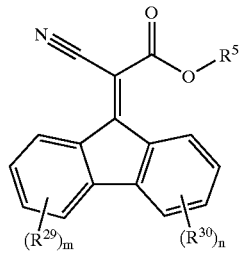

(XI)

wherein $R^5$ is selected from the group consisting of $C_1$–$C_{30}$ alkyl, $C_3$–$C_8$ cycloalkyl, substituted alkyl, hydroxyalkyl, substituted hydroxyalkyl, ether, substituted ether, substituted cycloalkyl, aryl, substituted axyl, and amino; $R^{29}$ and $R^{30}$ are the same or different and are selected from the group consisting of hydrogen, $C_1$–$C_{30}$ alkyl, $C_3$–$C_8$ cycloalkyl, substituted alkyl, hydroxyalkyl, substituted hydroxyalkyl, ether, substituted ether, ester, aryl, substituted aryl, hydroxyl, alkoxy, halogen, cyano, imide, urethane, amide, and amino; andm and n are each in the range of 0 to 4.

* * * * *

UNITED STATES PATENT AND TRADEMARK OFFICE
CERTIFICATE OF CORRECTION

| | | |
|---|---|---|
| PATENT NO. | : 6,919,473 B2 | Page 1 of 1 |
| APPLICATION NO. | : 10/458286 | |
| DATED | : July 19, 2005 | |
| INVENTOR(S) | : Craig A. Bonda et al. | |

It is certified that error appears in the above-identified patent and that said Letters Patent is hereby corrected as shown below:

In the Title: item 54 and Column 1

"PHOTOSTABILIZERS" should be --NOVEL PHOTOSTABILIZERS--.

In the Claims:

Claim 1, line 66, "cyoloalkyl" should be --cycloalkyl--,

Claim 6, line 21, "compxising" should be --comprising--,

Claim 6, line 17, "axyl" should be --aryl--,

Claim 6, line 22, "andm" should be --and m--.

Signed and Sealed this

Fourteenth Day of November, 2006

JON W. DUDAS
*Director of the United States Patent and Trademark Office*